United States Patent
Prerau et al.

(10) Patent No.: US 11,547,349 B2
(45) Date of Patent: Jan. 10, 2023

(54) SYSTEM AND METHOD FOR SPECTRAL CHARACTERIZATION OF SLEEP

(71) Applicant: THE GENERAL HOSPITAL CORPORATION, Boston, MA (US)

(72) Inventors: Michael J. Prerau, Watertown, MA (US); Patrick L. Purdon, Somerville, MA (US)

(73) Assignee: The General Hospital Corporation, Boston, MA (US)

(*) Notice: Subject to any disclaimer, the term of this patent is extended or adjusted under 35 U.S.C. 154(b) by 989 days.

(21) Appl. No.: 15/305,558

(22) PCT Filed: Apr. 28, 2015

(86) PCT No.: PCT/US2015/028046
§ 371 (c)(1),
(2) Date: Oct. 20, 2016

(87) PCT Pub. No.: WO2015/168152
PCT Pub. Date: Nov. 5, 2015

(65) Prior Publication Data
US 2017/0042469 A1 Feb. 16, 2017

Related U.S. Application Data

(60) Provisional application No. 61/985,169, filed on Apr. 28, 2014.

(51) Int. Cl.
*A61B 5/00* (2006.01)
*A61B 3/113* (2006.01)
(Continued)

(52) U.S. Cl.
CPC ............ *A61B 5/4812* (2013.01); *A61B 3/113* (2013.01); *A61B 5/0205* (2013.01); *A61B 5/11* (2013.01);
(Continued)

(58) Field of Classification Search
CPC ...... A61B 5/4812; A61B 5/4815; A61B 5/048; A61B 3/113
(Continued)

(56) References Cited

U.S. PATENT DOCUMENTS

2001/0031930 A1* 10/2001 Roizen ............... A61B 5/18
600/545
2002/0183644 A1* 12/2002 Levendowski ...... A61B 5/7207
600/544
(Continued)

FOREIGN PATENT DOCUMENTS

WO WO-0040148 A1 * 7/2000 ............. A61B 5/048

OTHER PUBLICATIONS

International Search Report and Written Opinion issued in corresponding International Application No. PCT/US15/28046, dated Aug. 12, 2015, 7 pages.
(Continued)

Primary Examiner — Gary Jackson
Assistant Examiner — Zahed Kabir
(74) Attorney, Agent, or Firm — Quarles & Brady LLP

(57) ABSTRACT

A system and method for identifying sleep states of a subject are provided. In some aspects, the method includes acquiring physiological data from a subject over a sleep period using sensors positioned about the subject, and assembling the physiological data into time-series datasets. The method also includes selecting a temporal window in which signals associated with the time-series datasets are substantially stationary, computing a time bandwidth product based on a selected spectral resolution and the selected temporal window, and determining a number of tapers using the computed time bandwidth product. The method further includes computing a spectrogram using the determined number of tapers and the time-series datasets, analyzing the spectro-
(Continued)

gram to identify signatures of sleep in the subject, and generating, using the identified signatures, a report indicative of sleep states of the subject.

21 Claims, 25 Drawing Sheets

(51) Int. Cl.
| | | |
|---|---|---|
| A61B 5/145 | (2006.01) | |
| A61B 5/11 | (2006.01) | |
| A61B 5/0205 | (2006.01) | |
| A61B 5/374 | (2021.01) | |
| A61B 5/389 | (2021.01) | |
| A61B 5/0533 | (2021.01) | |
| A61B 5/08 | (2006.01) | |

(52) U.S. Cl.
CPC .......... *A61B 5/14542* (2013.01); *A61B 5/374* (2021.01); *A61B 5/389* (2021.01); *A61B 5/4815* (2013.01); *A61B 5/7278* (2013.01); *A61B 5/0533* (2013.01); *A61B 5/08* (2013.01)

(58) Field of Classification Search
USPC .......................................................... 600/301
See application file for complete search history.

(56) References Cited

U.S. PATENT DOCUMENTS

| | | | | |
|---|---|---|---|---|
| 2005/0080828 | A1* | 4/2005 | Johnson | A61B 5/374 |
| | | | | 708/160 |
| 2006/0235315 | A1* | 10/2006 | Akselrod | A61B 5/02405 |
| | | | | 600/509 |
| 2009/0088658 | A1* | 4/2009 | Luo | A61B 5/369 |
| | | | | 600/544 |
| 2009/0203972 | A1 | 8/2009 | Heneghan et al. | |
| 2011/0301487 | A1* | 12/2011 | Abeyratne | G16H 50/50 |
| | | | | 600/544 |
| 2012/0029378 | A1 | 2/2012 | Low | |
| 2014/0180160 | A1* | 6/2014 | Brown | A61B 5/4821 |
| | | | | 600/544 |
| 2015/0088024 | A1* | 3/2015 | Sackellares | G06K 9/00523 |
| | | | | 600/544 |

OTHER PUBLICATIONS

Liu et al. "Large-Scale Spontaneous Fluctuations and Correlations in Brain Electrical Activity Observed with Magnetoencephalography" Neuroimage. May 15, 2010; 51(1): 102-111. doi:10.1016/j.neuroimage. 2010.01.092.

* cited by examiner

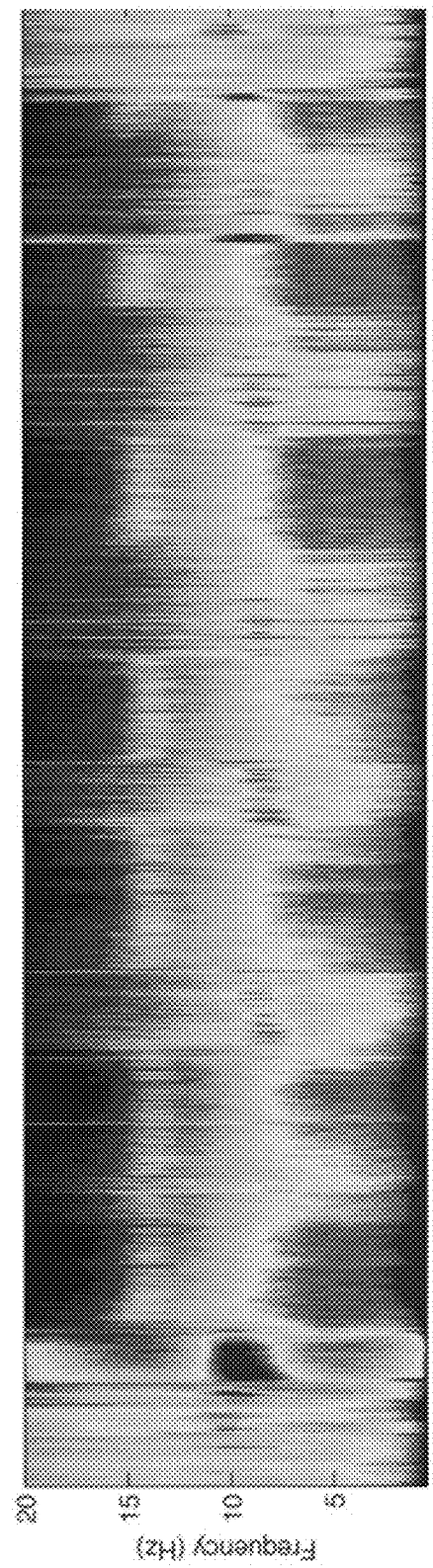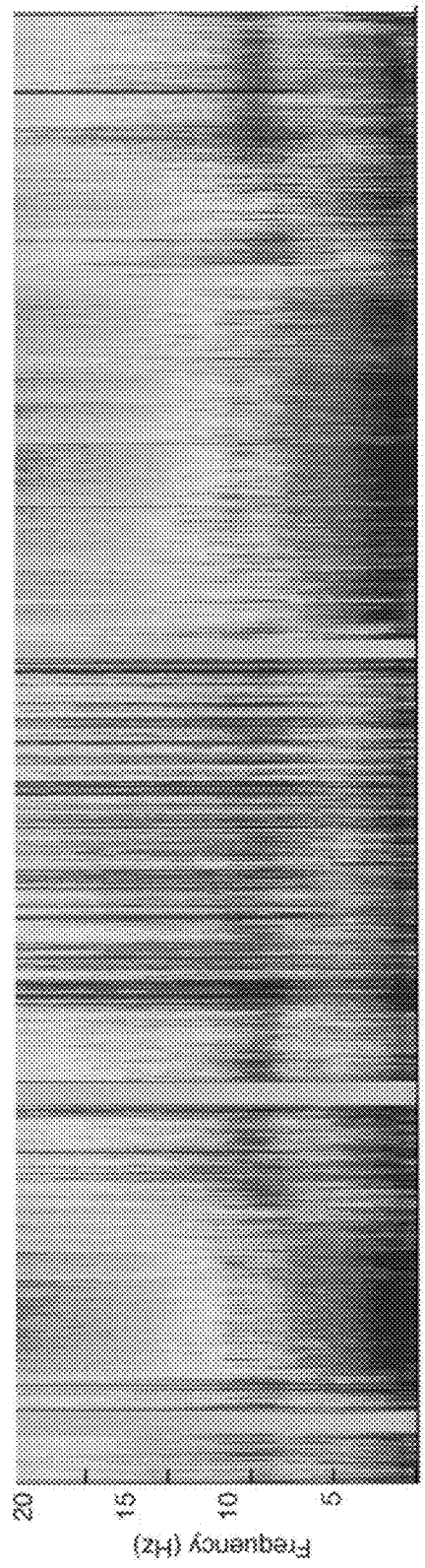

SYSTEM AND METHOD FOR SPECTRAL CHARACTERIZATION OF SLEEP

CROSS-REFERENCE TO RELATED APPLICATIONS

This application represents the U.S. National Stage of International Application No. PCT/US2015/028046, filed on Apr. 28, 2015 which claims the benefit of U.S. Provisional Patent Application Ser. No. 61/985,169, filed on Apr. 28, 2014, both of which are incorporated herein by reference for all purposes.

STATEMENT REGARDING FEDERALLY SPONSORED RESEARCH

This invention was made with government support under grant number OD006454 awarded by the National Institutes of Health. The government has certain rights in this invention.

BACKGROUND

The field of the invention is related to systems and methods for monitoring a subject. More particularly, the invention is directed to systems and methods for characterizing sleep states using physiological measurements.

Sleep is neural process consisting of multiple local and spatiotemporally-evolving factors, and direct observation of brain activity has been the primary means of characterizing sleep. Since the first recordings of brain activity using electroencephalogram ("EEG") data, scientists have sought to characterize the complex recurring patterns associated with sleep. Primarily, these patterns have been organized through the process of sleep staging, which is a rule-based categorization of sleep performed using visual inspection of the EEG time-series in non-overlapping epochs.

In the 1920s, Hans Berger, inventor of the EEG, first noted the difference between the sleeping and wake EEG, and observed the occipital oscillation in alpha (8-12 Hz). In the 1930s, Loomis, Harvey and Hobart incorporated the presence of spindles in the sigma band (12-15 Hz), and proposed a 5-stage categorization of sleep. In the 1950s, rapid eye movement ("REM") sleep was discovered by Aserinsky and Kleitman. These discoveries paved the way for the Rechtschaffen and Kales ("R&K") system in 1968 of categorizing sleep stages. In this system, EEG recordings were visually scored over 30-second epochs, differentiating the awake stage from a rapid eye movement ("REM") stage and four non-rapid eye movement ("NREM") stages of sleep. Almost 50 years later, R&K scoring remains the clinical standard for sleep medicine and sleep research, with the minor modification that reduces NREM sleep to three stages, namely N1-N3. This approach provides a manageable abstraction and discretization of the EEG activity observed during the sleep, allowing crude identification of major sleep landmark and instantaneous transitions during sleep.

Sleep staging is a time-consuming and subjective process, requiring technicians to visually evaluate hours of EEG waveforms in hundreds of non-overlapping 30-second epochs. In addition, inter-scorer variability remains an ongoing concern, producing appreciably different results depending upon the severity of the underlying sleep disorder physiology. In attempts to improve scoring accuracy, some approaches have to increase the number of scoring stages and used smaller data epochs. However, these have enhanced resolution scoring paradigms not been adopted in the field, in part because they are even more laborious to generate than the current standard and are of unproven utility.

Visual scoring is inaccurate in characterizing sleep due to the very nature of the process, which distills the spatiotemporally dynamic continuum of EEG oscillations into discrete, subjectively-defined stages, over each 30-second analysis window or epoch. A sleep stage is assigned using visually identified features in each given window according to the R&K scoring rules. The resulting progression of scored sleep stages as a function of time is called a hypnogram, and serves as the basis for numerous derivative clinical indices. In this way, sleep staging takes the information-rich, dynamic, and continuous process of sleep, and reduces it to a low-resolution, stationary, and discrete semantic summary. Therefore, no matter how sophisticated analysis techniques utilized, they are ultimately be limited when referenced back to the discretized semantic framework involved in visual scoring. This is because ultimately the resolution in visual sleep staging is limited to the qualitative features in the EEG that can be efficiently discerned and categorized by the human eye.

Therefore, given the above, there is a need for systems and methods for use in analyzing sleep. In particular, the ability to identify dynamical properties associated with the sleep data could provide critical insight into the neural processes occurring during sleep as well as pathophysiology, aiding in both diagnosis and in treatment.

SUMMARY

The present invention overcomes the drawbacks of aforementioned technologies by providing a system and method for characterizing sleep in a subject using physiological measurements, such as electroencephalogram ("EEG") measurements. In particular, a multitaper spectral analysis is described for identifying various signatures and characteristics of sleep. In stark contrast to the standard visual scoring of sleep, aspects of the present disclosure may be used to fully characterize sleep dynamics over sleep periods ranging from a full night (many hours), to ultradian (minutes), and micro-event (seconds) time scales. In addition, as will be appreciated, the present approach greatly improves on bias and variance problems inherent to standard spectral techniques that have prevented widespread use in sleep analysis.

In accordance with one aspect of the disclosure, a system for identifying sleep states of a subject is provided. The system includes a plurality of sensors configured to acquire from a subject physiological data associated with sleep, and a processor configured to assemble the physiological data received from the sensors over a sleep period into time-series datasets. The processor is also configured to select a temporal window in which signals associated with the time-series datasets are substantially stationary, compute a time bandwidth product based on a selected spectral resolution and the selected temporal window, and determine a number of tapers using the computed time bandwidth product. The processor is further configured to compute a spectrogram using the time-series datasets and the determined number of tapers, analyze the spectrogram to identify signatures indicative sleep states of the subject, and in some aspects generate, using the identified signatures, a report indicative of sleep states of the subject.

In accordance with another aspect of the disclosure, a method for identifying sleep states of a subject is provided. The method includes acquiring physiological data from a subject over a sleep period using sensors positioned about the subject, and assembling the physiological data into time-series datasets. The method also includes selecting a temporal window in which signals associated with the time-series datasets are substantially stationary, computing a time bandwidth product based on a selected spectral resolution and the selected temporal window, and determining a number of tapers using the computed time bandwidth product. The method further includes computing a spectrogram using the determined number of tapers and the time-series datasets, analyzing the spectrogram to identify signatures of sleep in the subject, and generating, using the identified signatures, a report indicative of sleep states of the subject.

The foregoing and other aspects and advantages of the invention will appear from the following description. In the description, reference is made to the accompanying drawings that form a part hereof, and in which there is shown by way of illustration preferred embodiments of the invention. Such embodiments do not necessarily represent the full scope of the invention, however, and reference is made therefore to the claims and herein for interpreting the scope of the invention.

BRIEF DESCRIPTION OF THE DRAWINGS

FIG. 15A shows a graphical example of chin electromyography ("EMG") activity captured using a multitaper spectrogram, in accordance with aspects of the present disclosure, during a waking stage.

FIG. 15B shows a graphical example of chin EMG activity captured using a multitaper spectrogram, in accordance with aspects of the present disclosure, during a REM sleep stage.

DETAILED DESCRIPTION

Figure 3:
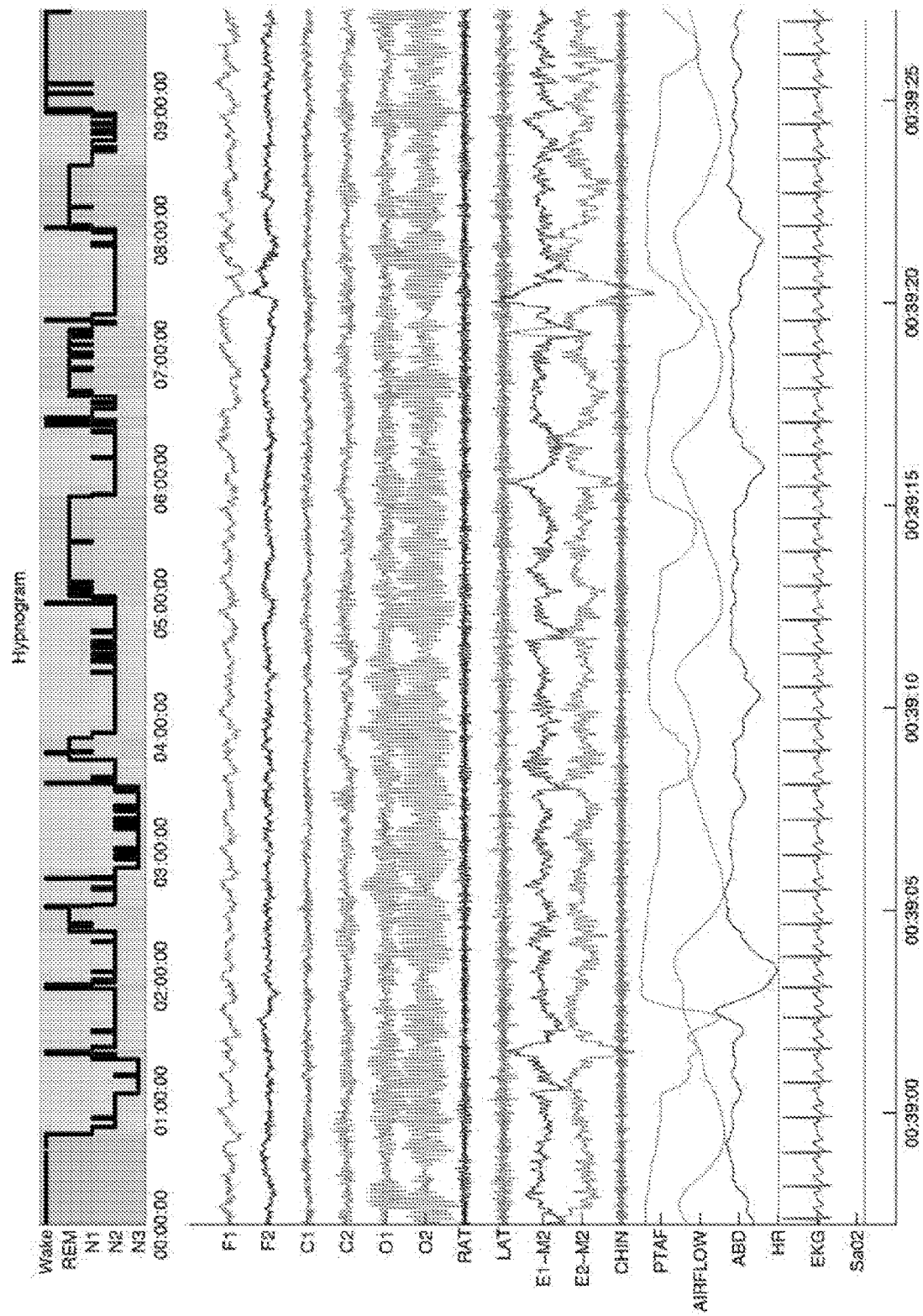
FIG. 3 is a graphical example showing a standard clinical sleep polysomnogram.

The Rechtschaffen and Kales ("R&K") system is the most common clinical method for analyzing sleep, visually differentiating sleep states into a waking stage, a rapid eye movement ("REM") stage, and three non-rapid eye movement ("NREM") stages, namely N1, N2, and N3, using electroencephalogram ("EEG") data acquired during the sleep process. FIG. 3 shows an example of a standard clinical sleep polysomnogram depicting sleep stages obtained using the R&K system. Although providing crude identification of major sleep stages, and assumed instantaneous transitions between them, along with EEG and other waveforms, such descriptions are inadequate in capturing the structure observed in the acquired EEG data. Specifically, sleep has been shown to be a continuous dynamic process involving the activity of numerous cortical and sub-cortical networks that evolve at different time scales, which cannot be appreciated from oscillatory waveforms shown in FIG. 3.

In order to overcome this drawback, some alternative scoring systems were introduced to include a finer resolution. For instance, one group characterized multiple physiological appearances of drowsiness in the EEG. Another proposed introducing 9 additional sleep stages between the waking state and stage 2 of NREM sleep. However, none of these approaches have enjoyed wide implementation, likely due to a combination of increased data processing times, and because such frameworks do not explicitly account for the diversity of normal variants, such as the absence of alpha EEG power during wakefulness in about 10% of the population. Moreover, they do not take into consideration individual variability associated with age, medications, or neurological disorders, and so forth.

Therefore, in order to accurately capture the dynamic structure of sleep, the present invention recognizes the importance of objective, quantitative analysis of sleep data rather than temporal and categorical discretization of sleep scoring. One alternative approach for analyzing sleep includes performing a spectral analysis using a time-frequency domain representation of the EEG waveforms, which categorizes contributions of oscillations at different frequencies to provide an objective, quantitative approach for understanding the structure of EEG. Typical spectral analyses employ a discrete Fourier transforms techniques, often used in conjunction with a tapering function and time-averaging to control the bias and variance of the spectral estimate (e.g. Welch, Hanning). The power within a specific band of interest is then typically averaged over a given analysis period, acting as the basis of comparative quantitative analyses.

While spectral analyses date back to the late 1980s and some have even been incorporated into some commercial clinical sleep staging programs, use of the spectrogram, referring to the visual representation depicting spectral power as a function of time, has not gained wide-spread use in sleep medicine. One likely reason is that previous methods were based on the Fast Fourier Transform ("FFT") techniques producing periodograms, or single-tapered spectral estimates, both of which produce estimates with a high variance and poor spectral resolution. As will be described, these representations are noisy and thus difficult to interpret.

Therefore, the present disclosure provides a system and method that implement a multitaper spectrogram approach for characterizing sleep, greatly improving upon the bias and variance problems inherent to standard spectral analyses. As will be described, application of the multitaper method to acquired physiological data, such as EEG data, makes clearly visible the relationships between spectral structure, traditional R&K scoring rules, and dynamics during a night of sleep that would be difficult to appreciate otherwise. Specifically, multitaper spectrograms can elegantly characterize the dynamics of the sleep EEG at full night (hours), ultradian (minutes), and micro-event (seconds) time scales.

As will be appreciated, the dynamic spectral motifs that encompass the Wake, REM, and NREM stages of sleep, and the transitions between them, are clearly detailed, such that it is possible to interpret overall ultradian dynamics up to a full night by computing a single multitaper spectrogram. Overall, the present disclosure demonstrates that multitaper spectrograms can provide a high-resolution, information-rich, multi-scale, estimates of non-stationary spectral dynamics of the sleep EEG data. In addition, by using multitaper spectrograms to characterize the sleep EEG, the continuous dynamics of multiple EEG oscillations are quantified and made visible in a way that current standard practice hypnogram representations cannot, while still making plain coarse features obtained using the R&K scoring system.

Figure 1A:
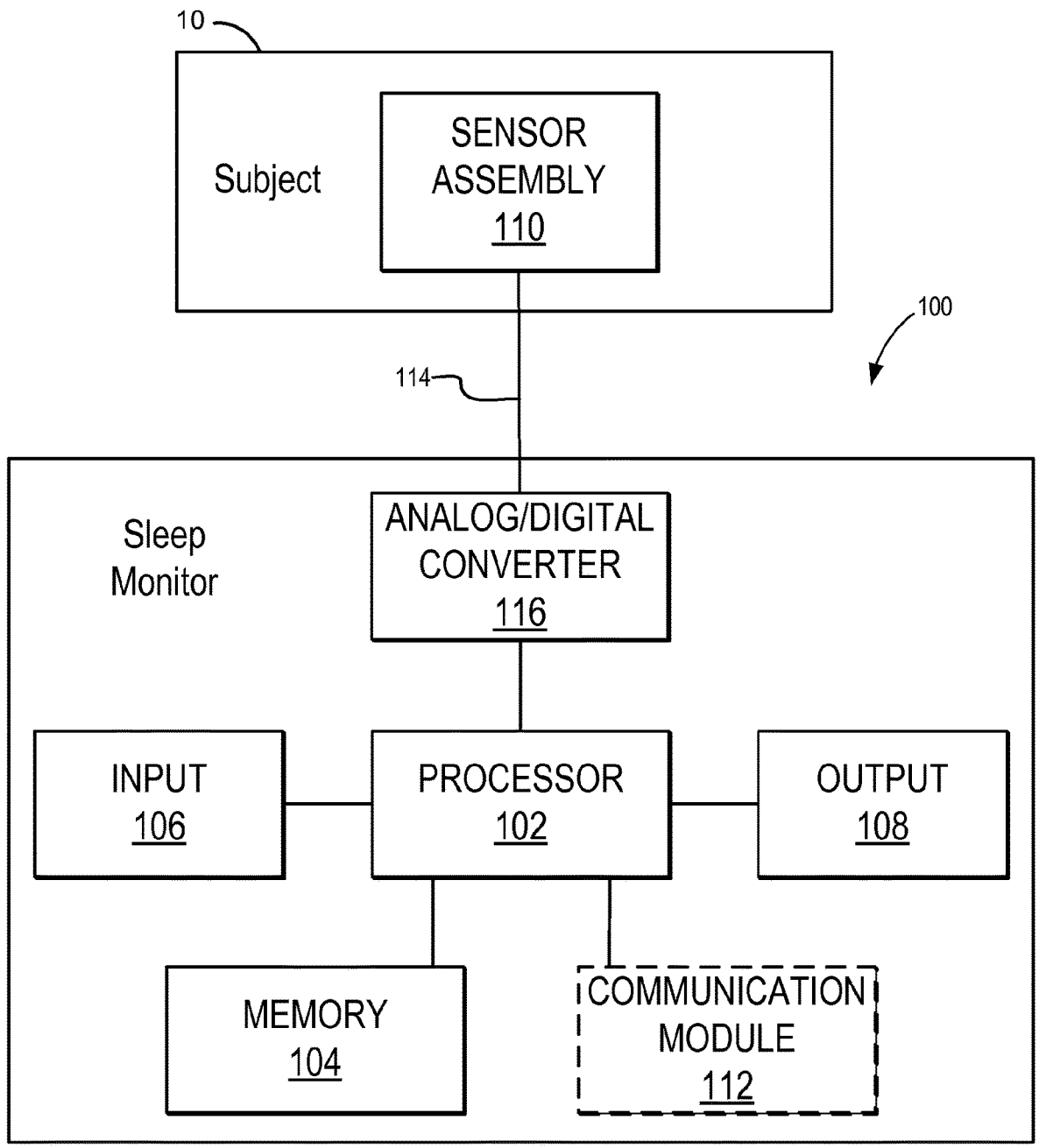
FIG. 1A is a schematic diagram showing an example sleep monitor, in accordance with aspects of the present disclosure.

Turning to FIG. 1A, a schematic diagram of an example sleep monitor 100 for use in characterizing sleep of a subject 10 is shown. In general, the sleep monitor 100 may be any device, apparatus or system capable of a wide range of functionality, integrating a variety of software and hardware capabilities. As shown in FIG. 1A, in some configurations, the sleep monitor 100 includes a processor 102, a memory 104, an input 106, an output 108, a sensor assembly 110.

Specifically, the sensor assembly 110 may include any number of sensing elements, and may be configured to measure a variety of signals associated with the subject 10, including brain activity, muscle activity, respiration activity, cardiac activity, eye movement, galvanic skin response, blood oxygenation, as well as motion, pressure, temperature, force, sound, flow, and so forth. In some implementations, as shown in the example of FIG. 1B, the sensor assembly 110 includes a plurality of EEG sensors configured to measure brain activity from multiple scalp locations about the subject 10.

For clarity, a single block is used to illustrate the sensor assembly 110 shown in FIG. 1A. However, it should be understood that the sensor assembly 110 shown can include more than one sensing element or sensing element types, such as electrical sensors, oxygenation sensors, galvanic skin response sensors, polysomnogram ("PSG") sensors, respiration sensors, muscle activity sensors, pressure sensors, force sensors, temperature sensors, air flow sensors, and so forth, and any combinations thereof. In addition, sensors may be placed at multiple locations about the subject 10, including, but not limited to, the scalp, face, nose, chin, skin, chest, limbs, fingers, and so on.

Figure 1B:
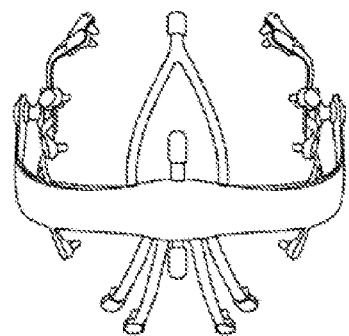
FIG. 1B is an example sensor assembly for acquiring electroencephalogram ("EEG") data, in accordance with aspects of the present disclosure.
Figure 1C:
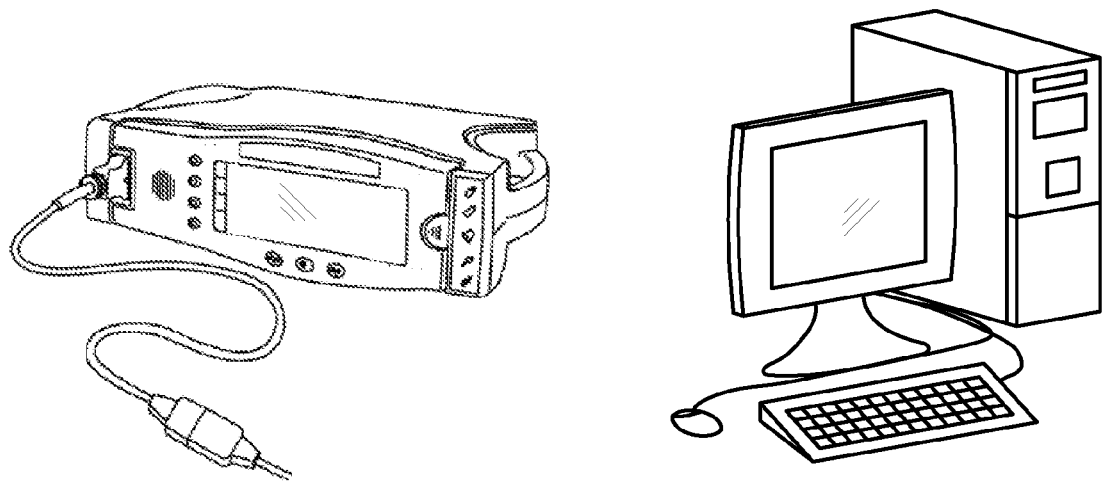
FIG. 1C shows non-limiting sleep monitor example embodiments, in accordance with aspects of the present disclosure.
Figure 1D:
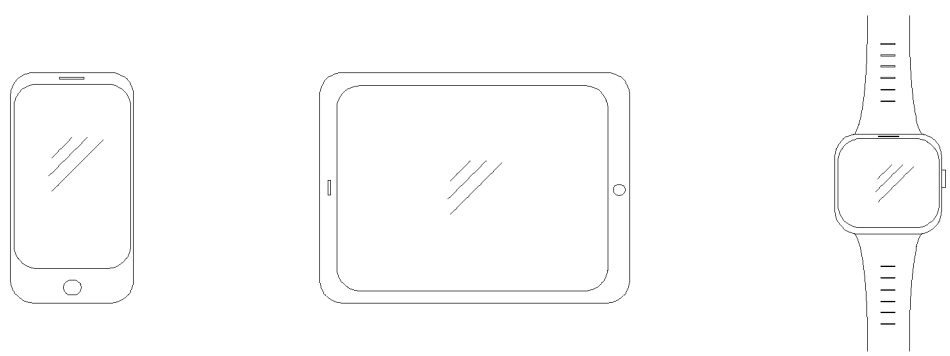
FIG. 1D shows additional non-limiting sleep monitor example embodiments, in accordance with aspects of the present disclosure.

The sleep monitor 100 may operate either independently or as part of, or in collaboration with any computer, system, device, machine, mainframe, database, server or network, as shown in the examples of FIG. 1B. In some aspects, the sleep monitor 100 may be a portable or wearable device or apparatus, for example in the form of a mobile device, tablet, smartphone, smartwatch, and the like, as shown in the examples of FIG. 1C. Alternatively, the sleep monitor 100 may be configured to communicate with such portable device or apparatus, for example, via a communication module 112, implementing a Bluetooth or other wireless communication protocol.

Signals generated by the sensor assembly 110 may then transmitted to the sleep monitor 100 over a cable or other communication link 114 or medium, digitized using the analog/digital converter 116, processed using one or more processor 102, and/or stored in memory 104. In some embodiments of the sleep monitor 100 shown in FIG. 1A, all of the hardware used to receive and process signals from the sensors are housed within the same housing. In other embodiments, some of the hardware used to receive and process signals is housed within a separate housing. In addition, the sleep monitor 100 of certain embodiments includes hardware, software, or both hardware and software, whether in one housing or multiple housings, used to receive and process the signals transmitted by the sensors.

The processor 102 may configured to carry out any number of steps for operating the sleep monitor 100. In addition, the processor 102 may be programmed to pre-process data obtained from the subject 10 using instructions stored in the memory 104. For instance, the processor 102 may configured to perform signal conditioning or pre-processing, such as scaling, amplifying, or selecting desirable signals, or filtering interfering or undesirable signals. In addition, the processor 102 may be configured to generate EEG sleep data using, for example, a scalp Laplacian montage, and/or perform a source localization analysis.

In accordance with aspects of the present disclosure, the processor 102 may be configured to assemble a time-frequency representation, in the form of multitaper spectrograms, using acquired EEG sleep data. In particular, the processor 102 may be configured to assemble the EEG data received from the sensors over a sleep period into time-series datasets, and select a temporal window in which signals associated with the time-series datasets are considered substantially stationary. The processor 102 may also be configured to compute a time bandwidth product based on a selected spectral resolution and the selected temporal window, and determine a number of tapers using the computed time bandwidth product. The processor 102 may then compute a multitaper spectrogram using the time-series datasets and the determined number of tapers.

In some aspects, the processor 102 may select, with or without user input, the multitaper spectrogram parameters based on context of the time-series datasets, for example, based on the time scale or context of the data. For instance, if sleep is being analyzed on a full night time scale, involving many contiguous hours, multitaper spectrogram parameters such as the temporal window length and time-bandwidth product can be chosen to capture the degree of temporal variation and spectral resolution visible and relevant on that time scale. Similarly, if sleep is being analyzed on an ultradian (about an hour) or micro-event (seconds) time-scales, different parameters can be used to emphasize the shorter time scale and/or transient nature of the events and features of interest. In some configurations, the processor 102 may be configured to adapt or modify the multitaper spectrogram parameters in substantially real-time, based on changes in data context or availability, or determine the multitaper spectrogram parameters based on a preset series of conditions stored in memory 104, a database or other storage medium. In addition, the multitaper spectrogram parameters may be selected based subject-specific factors, such as age or medical condition of the subject 10, such as mental illness or dementia. This is because the spectral dynamics can vary across different age groups as well as between healthy subjects and those with pre-existing medical conditions.

The processor 102 may be configured to analyze and identify signatures associated with data obtained from the subject 10 in order to characterize sleep dynamics and the onset of sleep. Specifically, the processor 102 may be configured to carry out sleep EEG spectral analysis using multitaper spectral estimation, autoregressive time series modeling, coherence analysis, global coherence analysis and so forth. Furthermore, the processor 102 may be configured to analyze specific events, features, time-scales, and frequency components of the data associated with different diagnostic features.

In some aspects, the processor 102 may utilize one or more generated multitaper spectrograms to identify specific signatures or signal features associated with particular stages of sleep. For instance, the processor 102 may utilize generated multitaper spectrograms with parameters optimized to identify arousals, spindles, K-complexes, and other features, or with parameters optimized to identify ultradian features. The processor 102 may also be configured to perform automatic detection of subject-specific stationary slow, alpha, and spindle peak oscillation frequencies. The processor 102 may also track over time subject-specific non-stationary frequency peaks including sigma, alpha, theta, and slow, and other signature oscillations. The processor 102 may also compute changes in the time constant in spectral power bands between different stages of sleep. The processor 102 may further utilize a multinomial model of sleep to estimate from EEG data one or more probability and uncertainty of a subject 10 being in a given state of sleep at a given point time. The processor 102 may also be configured to normalize spectral band power using data obtained from multiple subjects by using percentile-based normalization functions, including percentile-based indicator functions. In some aspects, identified signatures or signal features may be utilized to determine a sleep condition of a subject 10, or an effectiveness of an administered pharmacological agent on the sleep of the subject 10. The processor 102 may be further configured to determine a sleep fragmentation using computed spectrograms.

The processor 102 may be further configured to generate and provide a report either intermittently, or in real time, via output 108, which may include a display. The report may be any form, and include any information, including information related to acquired and processed physiological data, for instance as time-series waveforms or traces, time-frequency representations, power spectra, multitaper spectrograms, and so on. In some aspects, the report may include an indication or index related to the degree to which the subject 10 is awake at one or more points in time. Also, the report may include description regarding a state wakefulness or sleep of the subject 10. In other aspects, the report may characterize a sleep or sleep onset process. For instance, the report may include estimated probabilities, as well as confidence intervals thereof. The report may also include information regarding an identified sleep condition, effectiveness of an administered pharmacological agent. The report may also include information derived from a comparison between subject 10 data and data obtained from a population.

Figure 2:
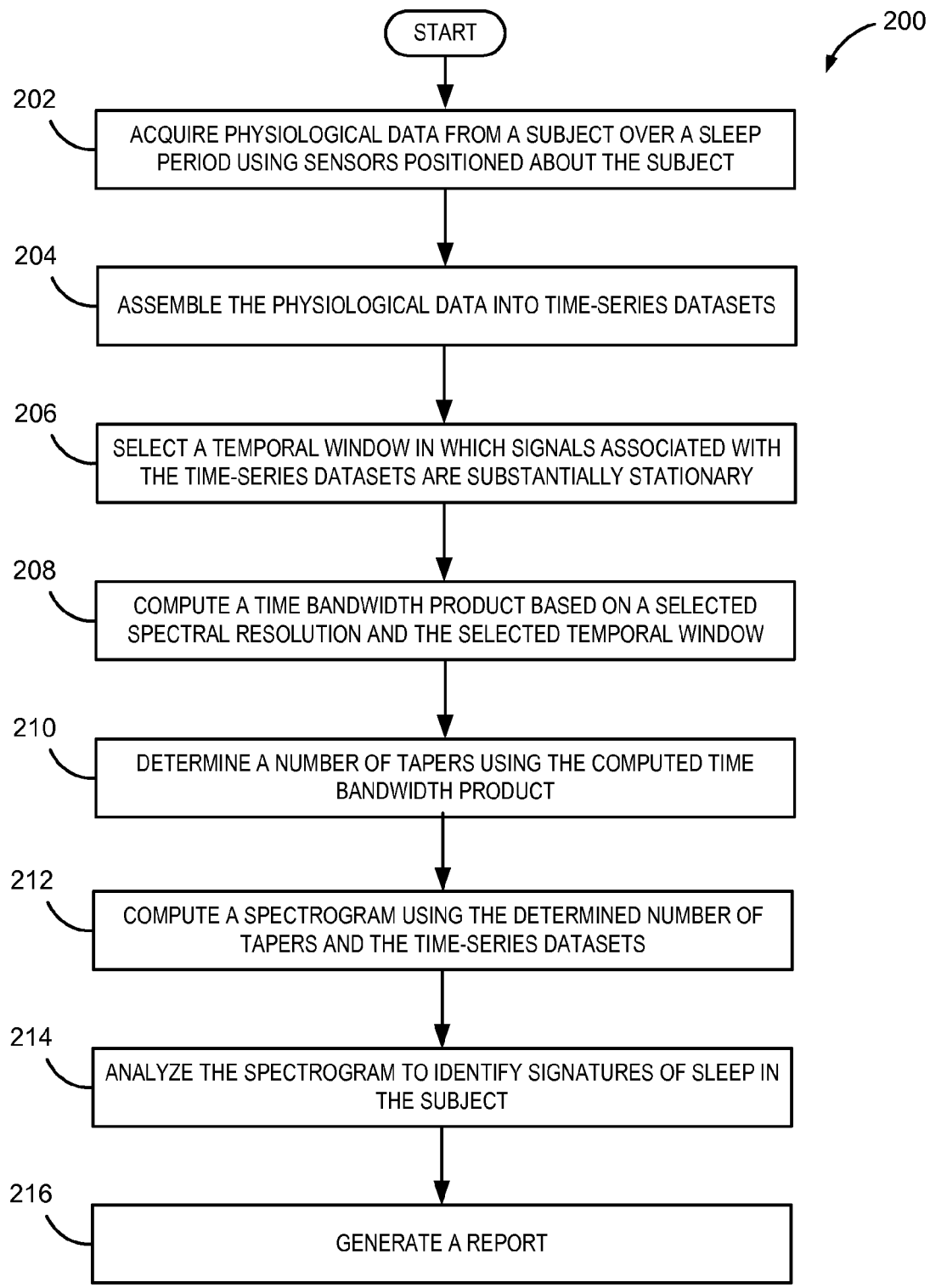
FIG. 2 is a flowchart setting forth steps of a process, in accordance with aspects of the present disclosure.

Turning to FIG. 2, steps of a process 200 in accordance with aspects of the present disclosure are shown, which may be carried out using any suitable system, such as the sleep monitor 100 described with respect to FIGS. 1A-1C. At process block 202 physiological data associated with sleep is acquired from the subject. As described, this step can include obtaining, using sensors positioned about the subject, any combination of measurements associated with physiological activity, including brain activity, muscle activity, respiration activity, cardiac activity, eye movement, galvanic skin response, blood oxygenation, and so forth. In some aspects, EEG data is acquired from a subject at process block 202 over a sleep period lasting a desired duration, such as a full night of sleep. Alternatively, rather than performing an acquisition step at process block 202, data may be retrieved from a local or remote storage location, memory or database at process block 202.

At process block 204 the acquired or retrieved physiological data may be assembled into time-series datasets. A temporal window may then be selected at process block 206, such that signals associated with the time-series datasets are considered substantially stationary. A time bandwidth product may then be computed using a selected spectral resolution and the selected temporal window, as indicated by process block 208.

At process block 210, a number of tapers may be determined using the time bandwidth product. Using the determined number of tapers, and the time-series datasets, one or more multitaper spectrograms may be computed at process block 212. Then, at process block 214, computed multitaper spectrograms may then be utilized to identify signatures of sleep in the subject. As described, this step can involve a number of processing steps and analyses, as detailed with regard to the processor 102 of FIG. 1A.

A report is then generated at process block 216. The report may be in any form, and can include information related to acquired and processed physiological data, for instance in the form of time-series waveforms or traces, time-frequency representations, power spectra, multitaper spectrograms, and so on. In some aspects, the report may include sleep probabilities, or may identify an onset of sleep. The report may track a drowsiness or wakefulness of a subject, or an effect of a pharmacological agent, or a change in sleep. The report may also characterize a sleep condition of the subject, such as insomnia or narcolepsy.

A goal of spectral estimation, sometimes referred to as spectral density estimation, is to decompose a waveform into its different frequency components. In general, spectral estimation takes any signal in the time domain (waveform traces as a function of time) and describes it in the frequency domain (spectral power as a function of frequency). The basis for spectral estimation most prevalently used is Fourier analysis, which is a method that decomposes a time-domain signal into a series of pure sinusoids. This is particularly useful in the analysis of EEG data, where the signal is composed of the activity of oscillating networks.

Figures 4A, 4B, 4C:
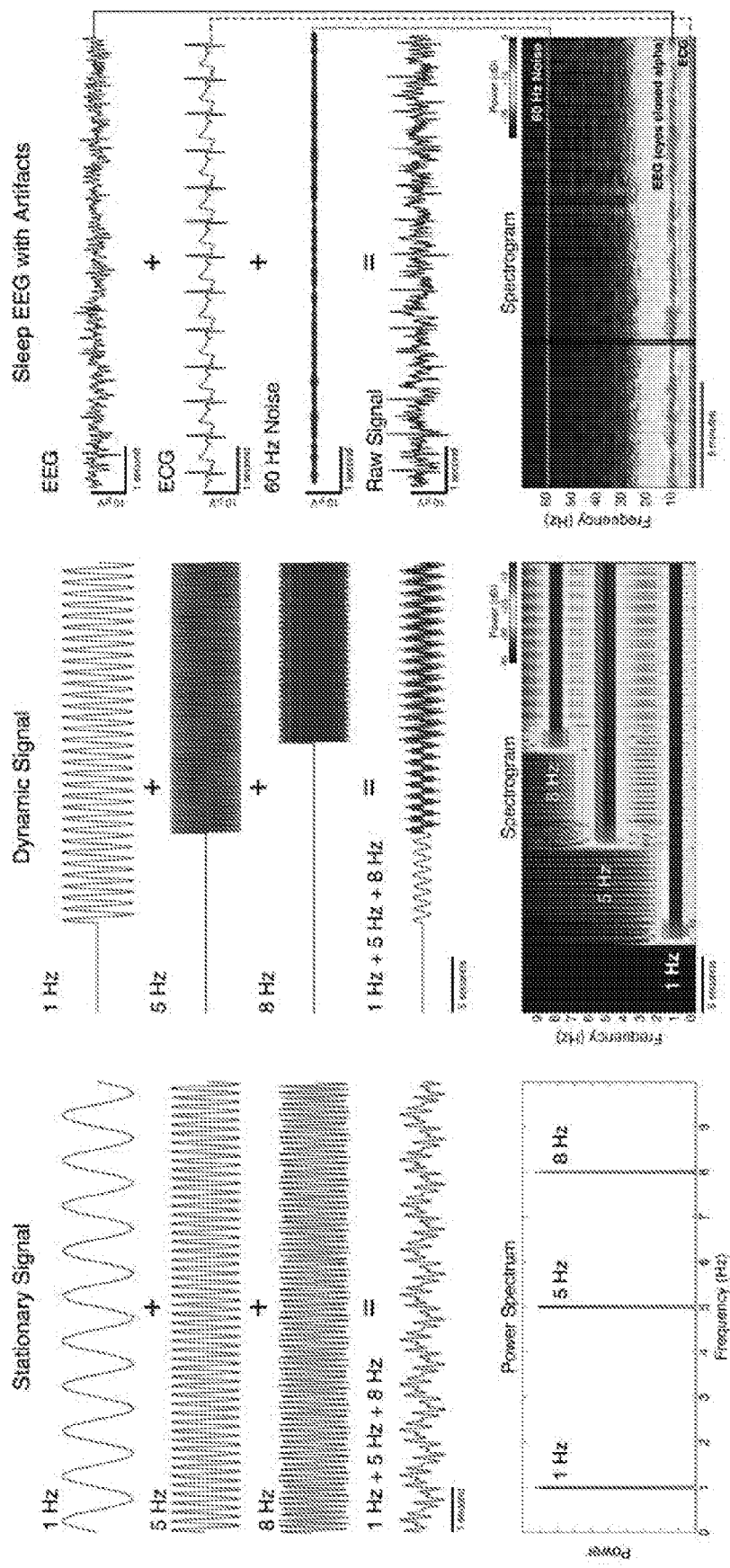
FIG. 4A is a graphical example illustrating the combination of stationary signals at different frequencies.
FIG. 4B is a graphical example illustrating the combination of dynamic signals at different frequencies.
FIG. 4C shows an example spectrogram obtained from sleep electroencephalogram ("EEG") data that includes confounding signals at different frequencies.

A stationary signal is one in which the oscillatory structure is invariant over time. In stationary signals it is appropriate to estimate a single power spectrum, which represents the power of the signal across different frequencies. FIG. 4A illustrates an example of how multiple stationary oscillatory signals combine into a single aggregate waveform with an intricate temporal structure. While the characteristics of the individual sinusoidal components are apparent when viewed separately, it is considerably more difficult to identify the number of underlying oscillations and their characteristics when viewing the aggregate waveform alone. By estimating the power spectrum of the signal, however, the number of oscillations, their frequencies, and their amplitudes become evident.

If a signal is dynamic, the oscillatory structure can vary over time, and is no longer stationary. Thus, if the intention is to characterize how oscillatory dynamics change in time, estimating a single power spectrum for the entire signal may not appropriate, as it will only show the average spectral structure across time. Instead, a spectrogram may be estimated for dynamic signals, which describes the spectral power as a function of frequency and time. A spectrogram may be constructed by estimating the power spectrum at different times using a temporal window of data. The size of such data window may be set such that the structure of the data within that time scale can be assumed to be stationary. A spectrogram may be visualized using an x-axis representing time, a y-axis representing frequency, and the spectral power represented by a color scale at each time-frequency point, as shown in the example of FIG. 4B. Specifically, FIG. 4B illustrates how multiple non-stationary oscillatory signals occurring at different points in time can combine into a single aggregate waveform. By computing the spectrogram of such aggregate waveform, the temporal dynamics of the oscillatory structure becomes apparent.

In the analysis of EEG data, dynamic spectral analysis has numerous benefits. FIG. 4C shows a real data example of typical EEG trace obtained during the early stages of the sleep onset process. While the goal may be to record only EEG data, it is common for other biological or external signals to corrupt a clinical recording. In this example, the raw signal contains the desired EEG data, but it also contains electrocardiogram ("ECG") activity as well as 60 Hz electrical noise. This makes the time domain signal much harder to read, and thus it is much more difficult to characterize the underlying EEG activity. Consequently, this segment of data would likely be seen as corrupted and thrown out, or filtering techniques might be applied in order to "clean up" the data. By using spectral analysis, however, no alteration of the data is necessary, as the components of the waveform reside at different frequencies. In the spectrogram the electrical noise is seen as a strong band at 60 Hz and the ECG artifact appears as a band between 1-2 Hz. The EEG signal appears as an evolving band at 10 Hz, which in this case represents the eyes closed alpha oscillation of the subject starting to fall asleep.

The most common method of spectral estimation is the periodogram, which uses the discrete Fourier transform ("DFT") as the basis function of spectral decomposition. The numerical method by which the DFT is computed is called the Fast Fourier Transform ("FFT"), and the periodogram is often simply referred to as the FFT. For a random signal $x_k$ sampled at intervals of $\Delta t$ where k=0, . . . , N−1, $\hat{S}_p(f)$, the periodogram at frequency f is defined as $$\hat{S}_p(f) = \Delta t \left| \sum_{k=0}^{N-1} x_k e^{2\pi i k f \Delta t} \right|^2. \quad (1)$$

Because of the finite duration of experimentally observed signals, the periodogram suffers from two potential problems. First, the spectral estimate is biased, namely on average, the periodogram will be different from the true underlying spectrum. The consequence of this bias is that peaks within the spectrum can appear less distinct and blurred across frequencies. In addition, the periodogram has high variance, due to the fact that the data is a single realization of a random signal. This produces noisy estimates of the spectrum.

In an effort to reduce the estimate bias, a common technique is to apply a taper or window to the data. Common tapers used are Welch, Hanning, and Hamming functions, which tend to limit the amount of bias or blurring. $\hat{S}_{tp}(f)$, the single-tapered periodogram at frequency f is defined as $$\hat{S}_{st}(f) = \Delta t \left| \sum_{k=0}^{N-1} w_k x_k e^{2\pi i k f \Delta t} \right|^2, \quad (2)$$

where $w_k$ is the value of the taper at time k.

While the single-tapered spectral estimate reduces the estimation bias as compared to the periodogram, commonly used tapers are not optimized for bias reduction and the variance of the spectral estimate is still high.

Given the high suitability of dynamic spectral analysis to characterizing sleep EEG, the reason why has it not yet taken hold in the field may lie in the fact that the most common techniques for spectral estimation produce noisy and biased estimates of the power spectrum, which makes it difficult to interpret the resulting spectrogram.

Therefore, in accordance with aspects of the present disclosure, a multitaper spectral estimation may be applied to sleep EEG data, an approach that reduces both the bias and variance of the resulting spectrum. This is achieved by averaging the estimates from multiple tapers applied to the same data window, which are optimized to limit bias. These tapers are called the discrete prolate spheroid sequences ("DPSS"), also known as the Slepian sequences, and have two special properties. First, the DPSS tapers are optimized to reduce both the broadening of peaks in the spectrum and blurring of power across frequencies. Second, DPSS tapers are orthogonal, which means they each extract independent estimates of the spectrum from the same window of data. In doing so, multiple estimates with reduced biased can be averaged together to produce a single estimate of the spectrum with reduced bias and variance.

Given a set of L tapers $\{w_k^1, \ldots, w_k^L\}$, $\hat{S}_{mt}(f)$, the multitaper spectral estimate at frequency f is defined as $$\hat{S}_{mt}(f) = \frac{1}{L}\left[\Delta t \left|\sum_{k=0}^{N-1} w_k^l x_k e^{2\pi i k f \Delta t}\right|^2\right], \quad (3)$$

in which the spectral estimate is the average of the single-taper estimates for each taper. It can be shown that the multitaper estimate reduces the variance by a factor of approximately L compared to single-tapered estimates.

In practice, the multitaper spectrum can be defined by three parameters, namely the size of the data window in seconds, N, the time bandwidth product, TW, and the number of tapers, L. Given these three parameters, the spectral resolution of the estimate may be defined as $$\Delta f = \frac{2TW}{N} \quad (4)$$

In some aspects, N may be chosen to be the length of time at which the data is assumed to appear stationary. Given N, TW can then be chosen to provide the desired spectral resolution. Given TW, it has been shown that a choice of $$L = \lfloor 2TW \rfloor - 1 \quad (5)$$

has desirable properties. For example, assuming that a given signal is stationary over 10 seconds, and for a desired spectral resolution of 1 Hz, $\Delta f=1$, N=10. Using (4) and (5), it then follows that $TW=N\Delta f/2=5$ and L=9.

Given sleep's continuous, dynamic nature, the ability to robustly distinguish signatures and changes thereof in the EEG spectrum is of vital importance in order to accurately characterize neural states at each point in time. As described, the large bias and variance inherent in standard FFT-based periodogram or single-tapered spectral estimates makes quantitative assessments of spectral dynamics difficult without averaging over large amounts of data, which may significantly reduce temporal resolution, and render inferences on individual patients or subjects impossible. Consequently, previous methods of sleep spectral analysis are not sensitive to important changes in the underlying neural activity.

Figure 5A:
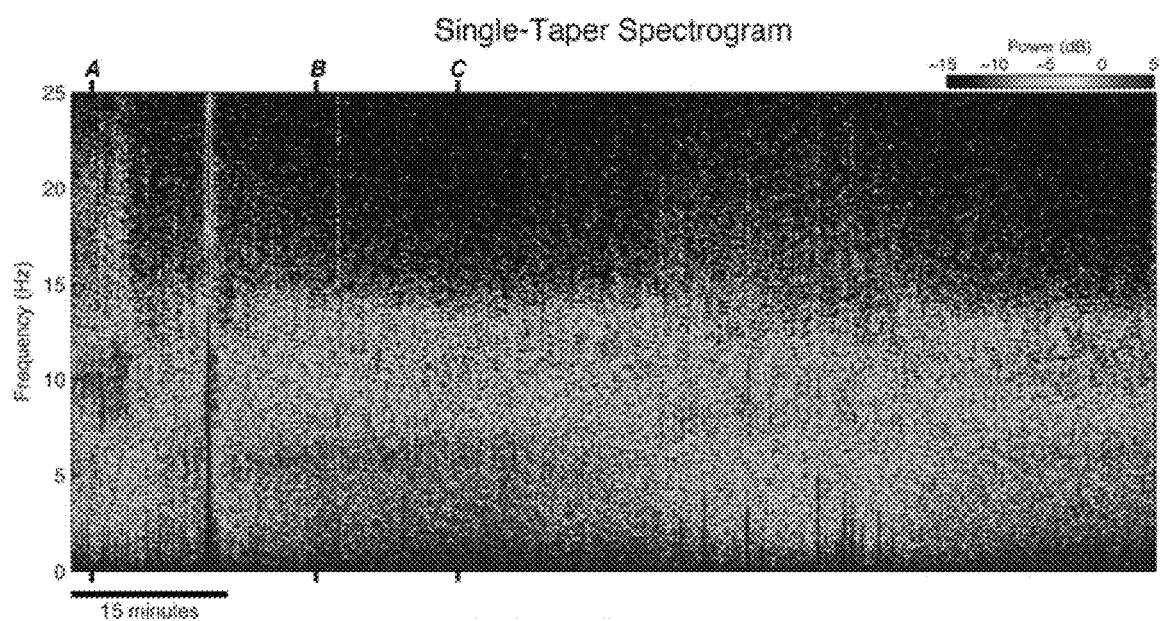
FIG. 5A is an example single-taper spectrogram.
Figure 5B:
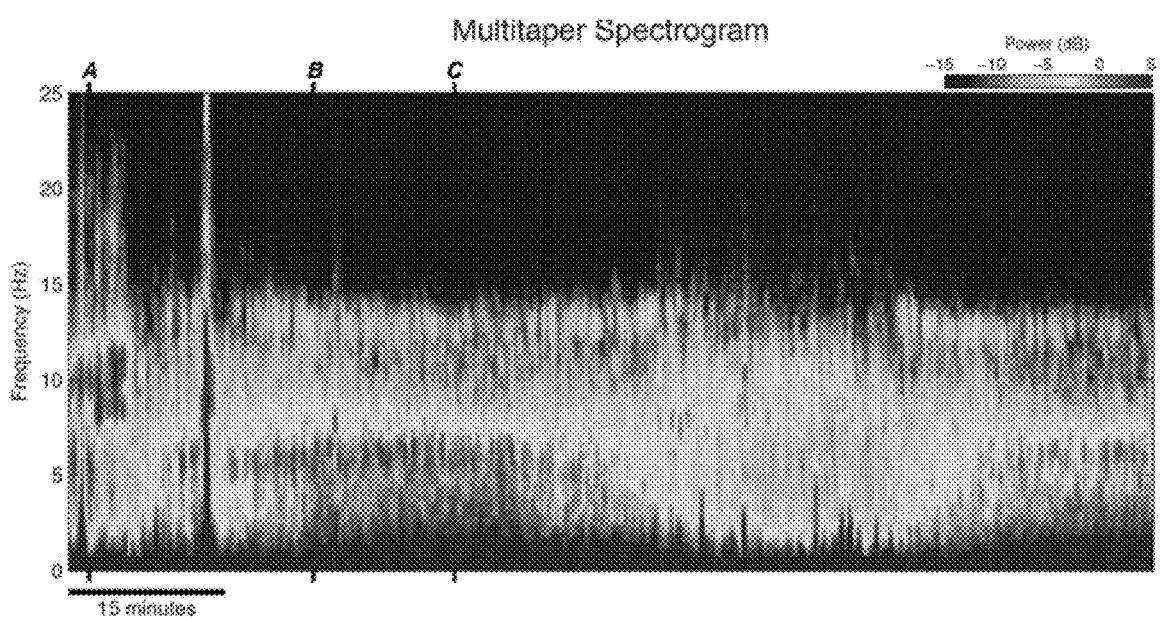
FIG. 5B is an example multi-taper spectrogram obtained using the same data as the single-taper spectrogram of FIG. 5A.
Figure 5C:
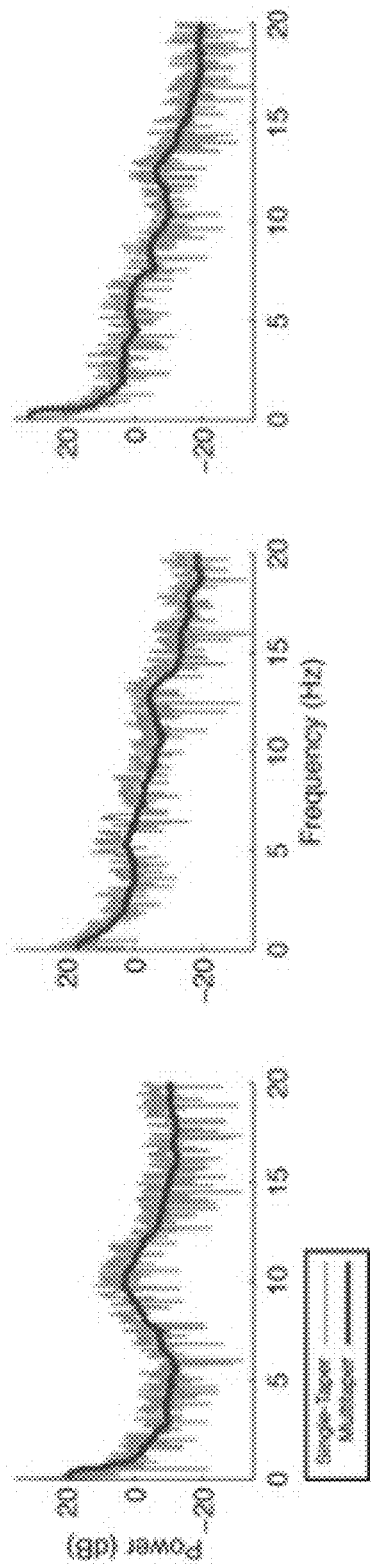
FIG. 5C is a comparison between spectra at different points in the spectrograms of FIGS. 5A and 5B, showing a significant improvement noise improvement for the multi-taper spectrogram of FIG. 5B.

By way of example, FIGS. 5A-5C show the difference between a single-taper Hanning window spectrogram, and a multitaper spectrogram, in accordance with the present disclosure, applied to a segment of occipital EEG data obtained during sleep. In comparison to the multitaper spectrogram shown in FIG. 5B, the single-taper spectrogram of FIG. 5A is very noisy, and difficult to clearly distinguish oscillatory dynamics across time. In contrast, the multitaper spectrogram shows a dynamic interplay of neural oscillations with clearly defined peaks during this time period. The reason for this difference is made even more apparent by examining the power spectrum. Specifically, FIG. 5C shows the single-taper and multitaper spectral estimates at time points corresponding to wake (marker A), Stage N2 (marker B), and Stage N3 (marker C). In all cases, the single-taper estimates have high variability and a coarse structure, in comparison to the multitaper estimates, which are smooth and have clearly defined spectral peaks.

To illustrate the point further, a bootstrap analysis was performed to quantitatively demonstrate the improvement of the present multitaper method in identifying key features of the sleep EEG over standard methods. In particular, the two major traditional phases of sleep, namely NREM and REM, were analyzed. In order to compare the EEG spectra under two different conditions, a bootstrap procedure was used to estimate the probability distribution of difference in the spectrum between the two conditions, which then allows identification of significant spectral differences between the conditions. Specifically, spectra from each of the conditions were first selected and the difference in power at each frequency was computed. By repeating this procedure many times, it was possible to build a distribution of the spectral difference between the two conditions. Once the difference distribution was estimated from the bootstrap samples, the frequencies at which its 95% confidence intervals fell outside of 0 were said to differ significantly between the two conditions. FIGS. 6A-B and 7A-B depict example results from applying such bootstrap procedure to data acquired during NREM and REM stages, respectively, illustrating how the present multitaper approach is able to distinguish between changes in sleep state where standard periodogram methods are not.

Figure 6A:
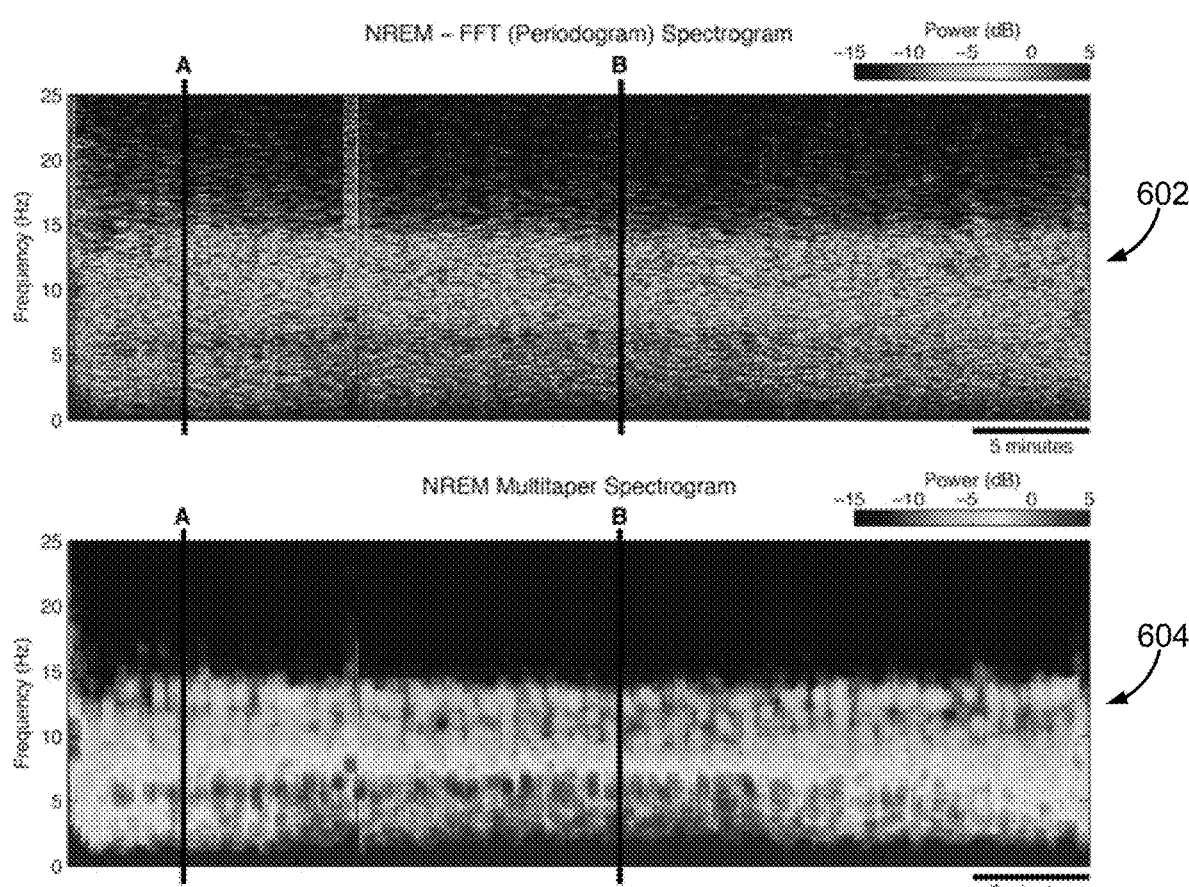
FIG. 6A is a graphical example comparing non-rapid eye movement ("NREM") data assembled using a periodogram and a multitaper spectrogram, in accordance with aspects of the present disclosure.
Figure 6B:
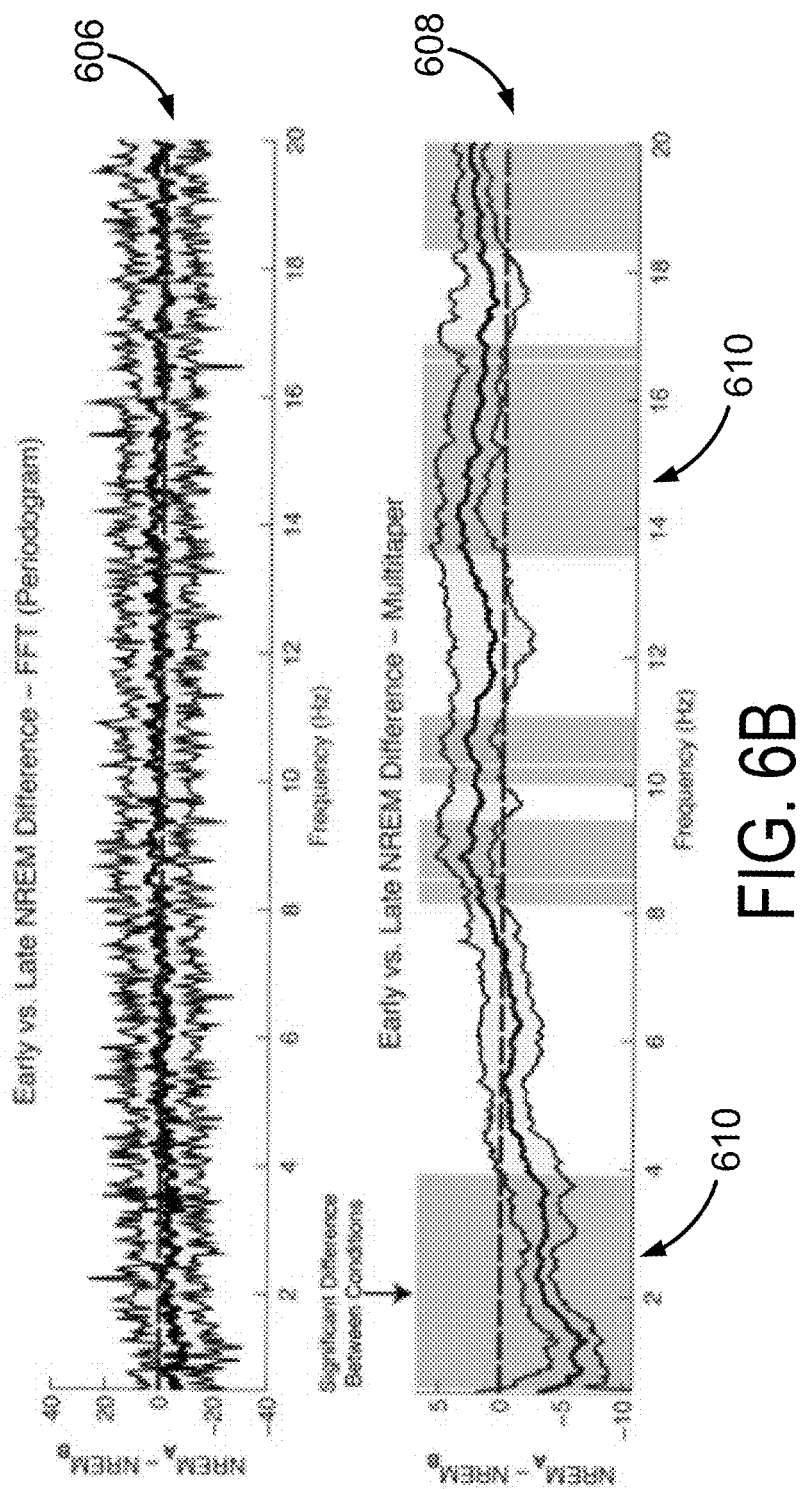
FIG. 6B is a graphical example obtained using a bootstrap analysis, illustrating quantitative differences between the periodogram and multitaper spectrogram of FIG. 6A.

Referring to FIGS. 6A-B, the degree to which the FFT (periodogram) and multitaper method could quantitatively identify changes in depth of NREM sleep. It has been long known, from studies averaging over many epochs of data across multiple cycles of sleep in many study subjects, that there are changes in the EEG spectra as NREM sleep progresses, including an increase in power in the slow-delta range (<5 Hz) as well as decreases in alpha (8-12 Hz) and sigma power (12-15 Hz). The ability to quantitatively identify these changes in spectral power in individual patients at particular points in time during a given night of sleep is therefore important for monitoring dynamics in depth of NREM sleep.

The FFT periodogram 602 and multitaper spectrogram 604 were computed for a period of NREM sleep. Without any quantitative analysis, it is clear that the periodogram estimate is much noisier than the multitaper estimate, and that distinct spectral peaks, which correspond to oscillations in the time-domain EEG waveform, are much more difficult to see. For the quantitative analysis, two time points, namely A and B, were selected from light and deep NREM, respectively. The above-described bootstrap analysis was then performed, comparing a 2-minute window of data centered on each time point (FIG. 6B), computing the difference distribution for A (early NREM)–B (late NREM) for the periodogram 602 and multitaper spectrogram 604 estimates.

As appreciated from FIG. 6B, the periodogram difference graph 606 shows no significant differences between the early and late NREM periods, which would falsely suggest that there is no change in brain-state as NREM progresses. In contrast, the multitaper difference graph 604 shows multiple, clear regions 610 of significant differences, quantitatively indicating that slow-delta (<5 Hz) power is significantly increased in late NREM while and alpha (8-12 Hz) and sigma (12-15 Hz) are significantly decreased.

Figure 7A:
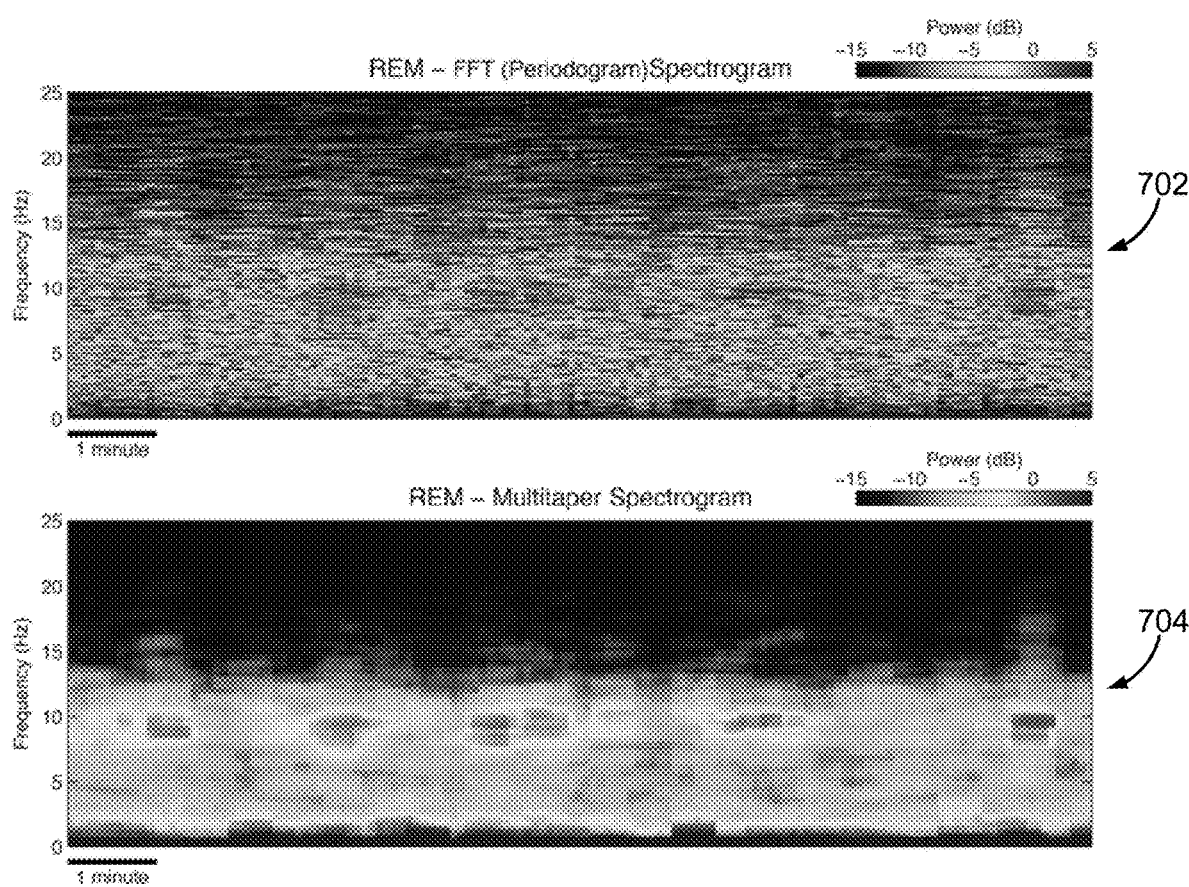
FIG. 7A is a graphical example comparing rapid eye movement ("REM") data assembled using a periodogram and a multitaper spectrogram, in accordance with aspects of the present disclosure.
Figure 7B:
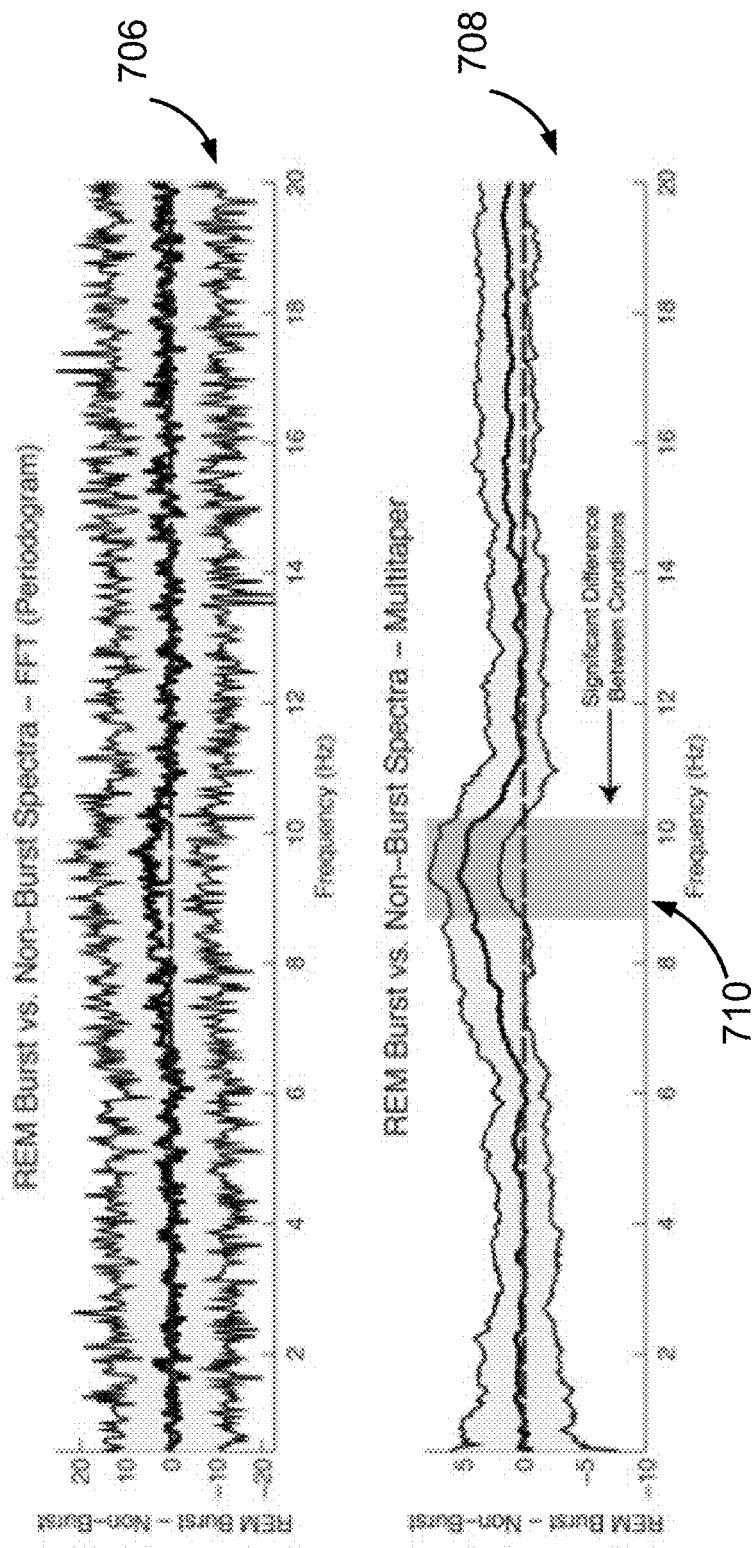
FIG. 7B is a graphical example obtained using a bootstrap analysis, illustrating quantitative differences between the periodogram and multitaper spectrogram of FIG. 7A.

As a second example, shown in FIGS. 7A-B, the ability of the FFT periodogram 702 and multitaper spectrogram 704 (FIG. 7A) quantitatively identify transient spectral peaks in the EEG spectrum during REM sleep was evaluated. Using the multitaper spectrogram 704, recurrent transient (5-10 seconds long) increased power in low alpha (7-9.5 Hz) extending throughout the peri-REM period—beginning in late NREM and continuing past traditionally scored REM, were identified. Such peri-REM alpha bursts have not been previously reported using standard spectral analysis techniques, likely due to the high noise in the periodogram estimates, which would obscure brief spectral changes occurring during REM. For a small epoch of REM, the difference between the burst and non-burst spectra was then examined using the above-described bootstrap procedure.

Similar to the NREM example, the FFT periodogram 702 was much noisier than the multitaper spectrogram 704, with the bounds of the transient alpha bursting being much more difficult to identify visually. In this case as well, the bootstrap procedure, using the estimates shown in FIG. 7A, showed no significant difference between the bursting and non-bursting spectra. This can be appreciated from periodogram difference graph 706 of FIG. 7B. Consequently, use of periodogram 702 would falsely suggest that there was no change in brain-state. The multitaper difference graph 708, on the other hand, did show a clear region 710 of significant difference around 9 Hz, which is the central frequency of these particular bursts.

The above examples show, in a quantitative manner, a vast improvement in the ability to distinguish differences in EEG spectra that the present multitaper approach has over standard FFT-based methods. Thus, by using the multitaper spectrogram in sleep EEG analysis, the dynamic changes in brain state that occur during sleep can be captured and characterized.

The above-described system and method may be further understood by way of example. This example is offered for illustrative purposes only, and is not intended to limit the scope of the present invention in any way. Indeed, various modifications of the invention in addition to those shown and described herein will become apparent to those skilled in the art from the foregoing description and the following example, and fall within the scope of the appended claims.

EXAMPLE

Multitaper spectrograms were constructed by estimating the multitaper spectrum in each of a set of data segments of fixed size, overlapped for increased temporal continuity. By changing the parameters, spectrograms were designed for obtaining clarity at different times scales. Specifically, data from full-night, ultradian, and micro-event time scales were analyzed, choosing parameters according to each scale. Specifically, the multitaper parameters were TW=15, L=29, N=30 s, overlap 5 s for the full-night spectrograms, TW=3, L=5, N=6 s, overlap 0.25 s for the ultradian spectrograms, and TW=5, L=9, N=2.5 s, overlap 0.05 s for the micro-event spectrograms.

Data from ten healthy right-handed subjects (5 women and 5 men) with ages ranging 19-32 years (mean: 25.8, std: 5.09) and BMI<30, were obtained from two consecutive nights. Subjects were pre-screened to ensure a regular sleep schedule and no history of sleep disorder, psychiatric problem, or neurological disease, as well as to ensure no history of tobacco, or prescription/recreational drug use. One night of home monitoring was performed prior to the lab testing to exclude obstructive sleep apnea ("OSA") screening (using a threshold of AHI<5, and RDI<15) (WatchPAT, Itamar Medical). In addition, an experienced technician scored the experimental polysomnogram ("PSG") data following the first experimental night, and one subject was excluded after failing to meet the OSA criteria on the first night. Urine tests for drug use (Xalex Multi Drug Kit for 10 Drugs) were performed at screening and prior to each experimental night. Additionally, female subjects were screened for pregnancy.

Subjects were fit with a high-density (64-channel) EEG cap, as well as standard clinical PSG sensors including PTAF, airflow, abdominal belt, and eye, chin, and limb electrodes. Visual staging of sleep data was performed prior to the statistical analysis by an experienced clinical sleep technician using contemporary AASM guidelines.

The multitaper spectrogram provides a clear representation of the spectral dynamics of the sleep EEG occurring at time scales ranging from seconds to multiple hours. In what follows, representative examples of the sleep EEG from young, healthy subjects at the full night, ultradian, and micro-event time scales are shown. The most common progression of spectral dynamics observed in each distinct phase of sleep is described. While this is by no means an exhaustive atlas of the multitaper sleep EEG spectrogram in all of its incarnations, this work provides a framework of normative data, which can serve as a baseline for subsequent analyses of different populations and pathologies.

Figure 8A:
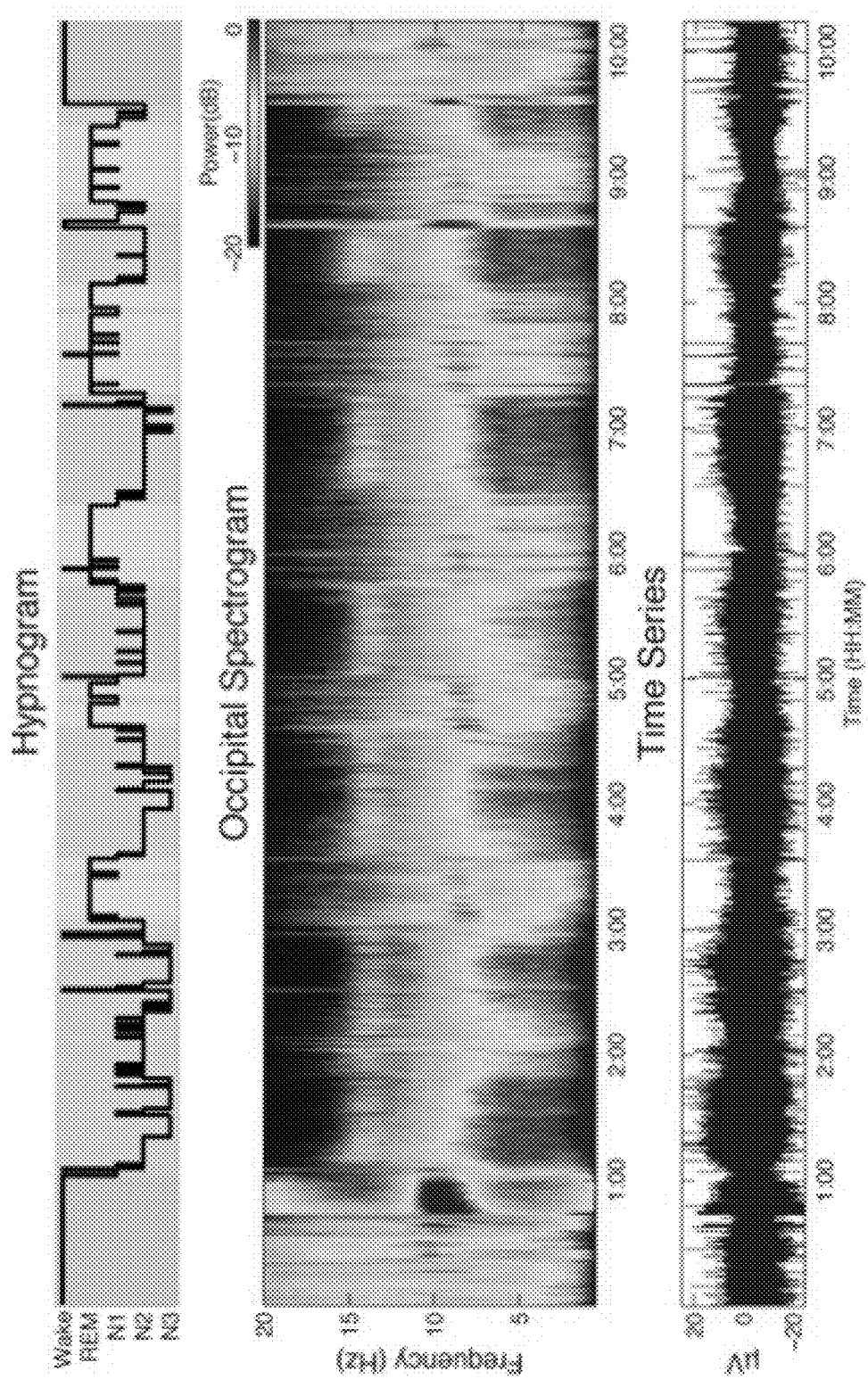
FIG. 8A is a graphical example illustrating spectral dynamics across a full night of sleep.
Figure 8B:
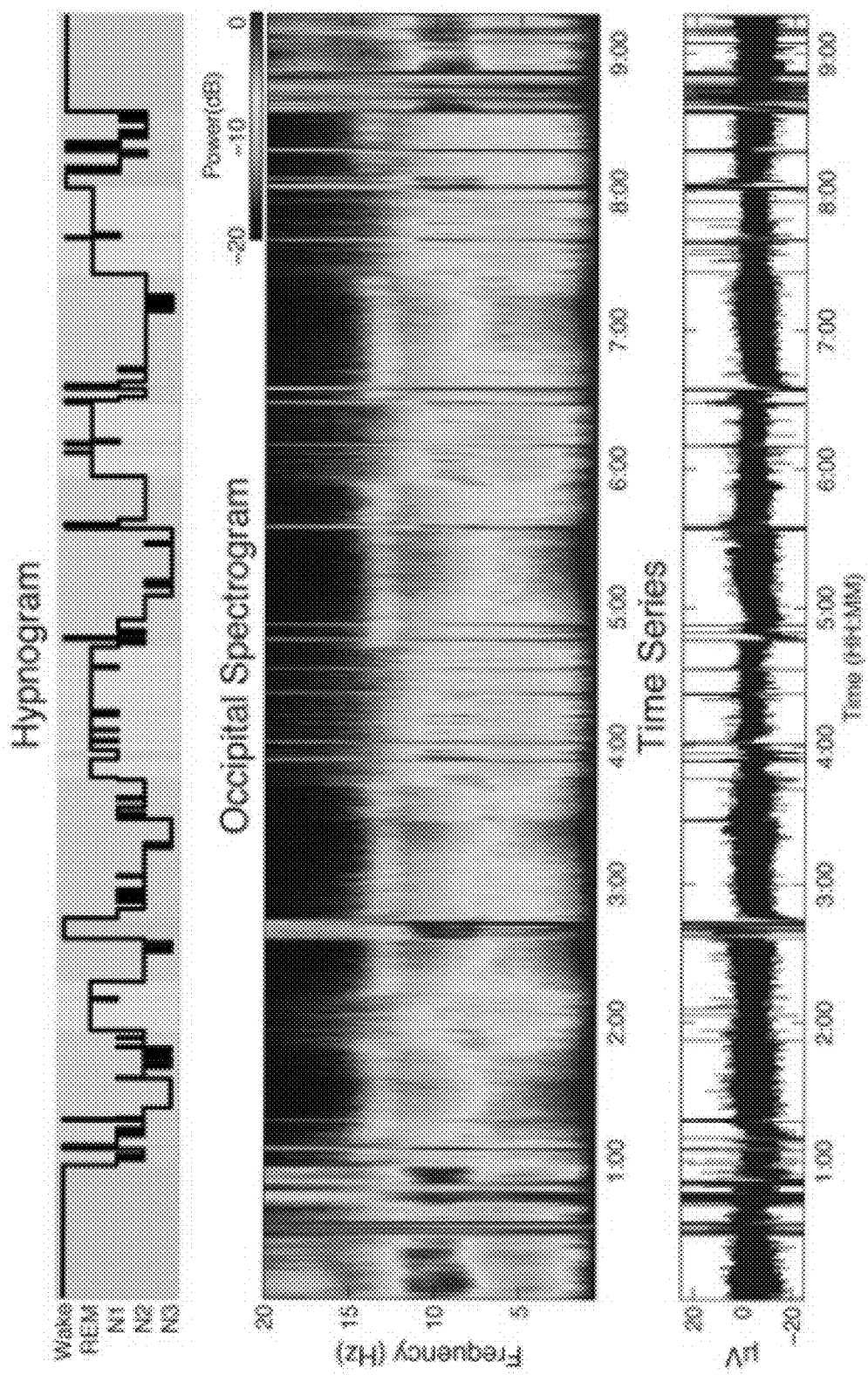
FIG. 8B is another graphical example illustrating spectral dynamics across a full night of sleep.

One of the primary benefits of using the multitaper spectrogram is the ability to observe EEG dynamics across an entire night in a single visualization. While the features required to visually score EEG time traces become effectively unreadable at a time scale of only a few minutes, the spectral dynamics of the sleep EEG can be clearly observed over a time scale of many hours. FIG. 8A-B show the occipital multitaper spectrogram of the sleep EEG of two different subjects (middle panels), along with the visual scored hypnogram (top panels) and time domain traces (bottom panels). Even without knowledge of the sleep EEG, it is possible to discern repeating multi-oscillation spectral motifs in the dynamic structure of the full night multitaper spectrogram, which correspond well with the overall hypnogram architecture. In contrast, the time domain traces at this scale show fluctuations in EEG amplitude, providing only a single dimension of information.

At the coarsest level, sleep is traditionally segmented into periods of Wake, REM, and NREM, the constituent components of the ultradian cycle. For the sake of simplicity, current clinical practice defines Wake and REM as unitary states, and NREM is divided into three discrete stages. By contrast multitaper spectrograms described herein make plain the continuum of changes within and between each of these states. For comparison, the EEG components used in traditional scoring are also represented in the time-frequency domain as a baseline of equivalence between the different methods.

The act of falling asleep is a continuous, dynamic, multifocal neural process, with behavioral and physiological changes occurring with different dynamics throughout the period of sleep onset. The most prominent hallmark of the sleep onset process is the appearance of a strong occipital oscillation in the alpha (8-12 Hz) band upon the closing of eyes during wakefulness, present in 90% of adults. As a subject falls asleep, the occipital power in alpha power gradually decreases, then becomes transient, and then disappears. The disappearance of alpha, which signifies scored Stage N1 sleep, initiates the potential for a rise in power in delta (0.5-4 Hz) and theta (4-8 Hz) bands. Should the subject be aroused or wake up, the process rapidly reverses, with power in delta and theta giving way to power in alpha.

Figure 9A:
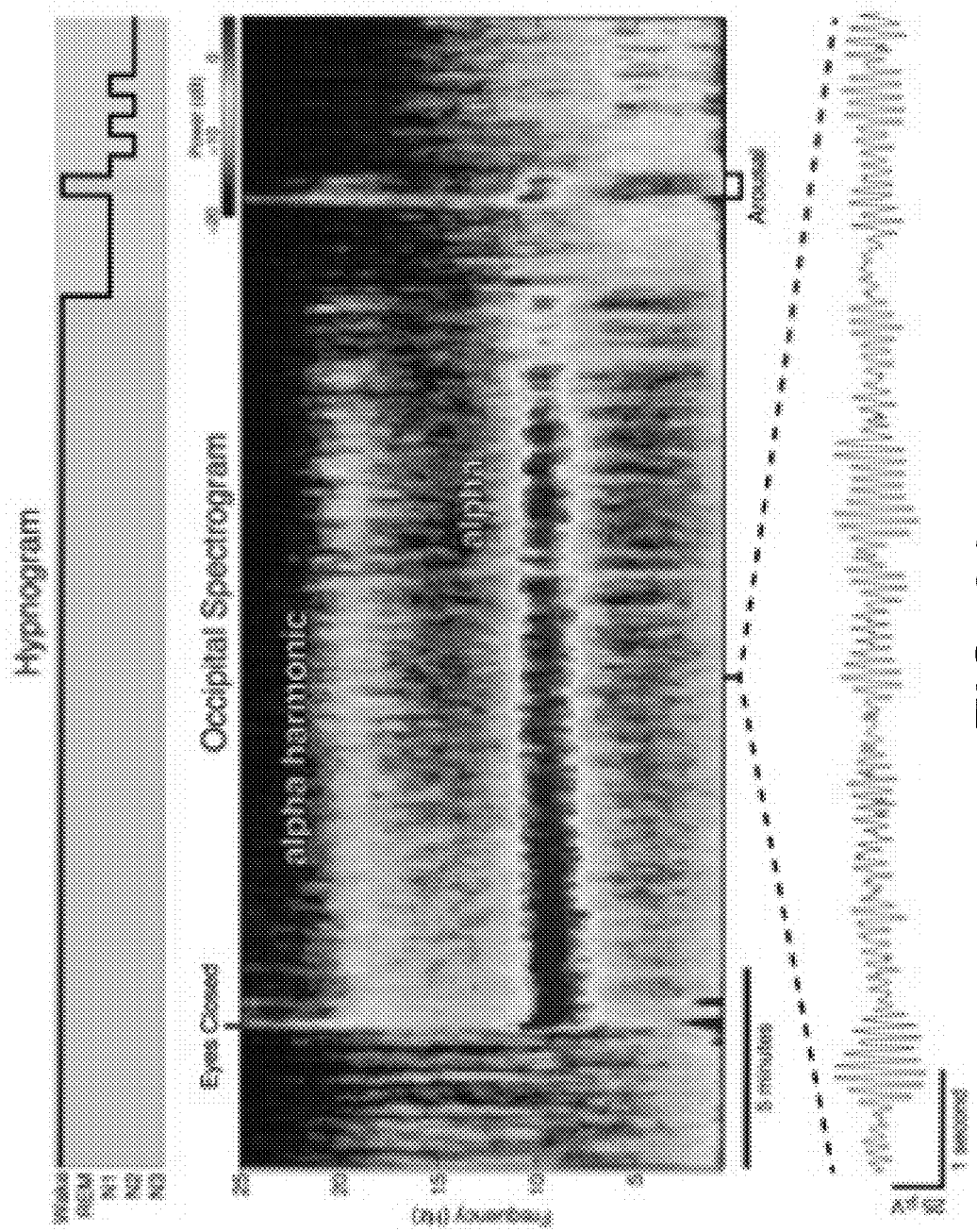
FIG. 9A is a graphical example illustrating spectral dynamics during initiation of the sleep onset process.

The spectral dynamics of wakefulness and sleep onset are illustrated in FIG. 9A, which shows the occipital multitaper spectrogram from a subject during the start of the sleep onset period. Initially, when the subject is quiescent with open eyes, the spectrogram has low power across all frequencies. When the subject's eyes close, the spectrogram changes dramatically, showing strong spectral power in alpha with a central frequency at approximately 9 Hz. Due to the imperfect sinusoidal structure of the alpha oscillation, it is also common to observe spectral power at the second alpha harmonic, which is two times the central frequency of the alpha oscillation. In this case, the alpha harmonic appears at approximately 18 Hz. As the sleep onset period progresses, the oscillation power and bandwidth in alpha gradually decrease, then fluctuate, then disappear.

The disappearance of alpha aligns well the start of technician scored Stage N1. With the loss of power in alpha, the spectrogram shows a broadband increase in power over delta and theta. The sudden subsequent disappearance of the power in delta/theta and reemergence of power in alpha signifies an arousal to wakefulness, which also aligns well with the hypnogram. The spectrogram then shows a reversal back to a high delta/theta state without power in alpha, indicating that the subject has fallen back to sleep. Thus, by understanding the meaning of these spectral motifs, it is possible to characterize the sleep onset dynamics of this subject with a single visualization.

Figure 9B:
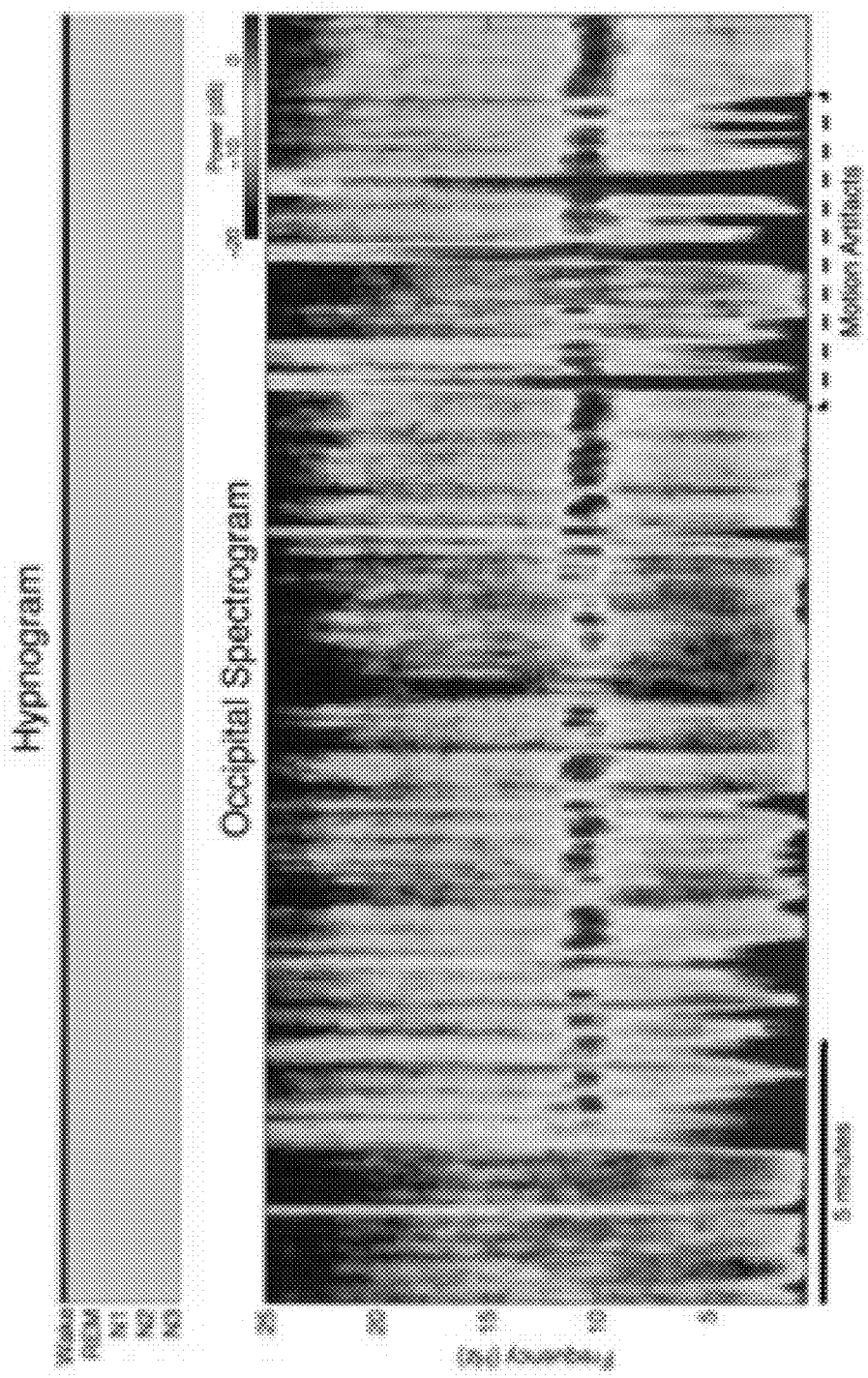
FIG. 9B is a graphical example illustrating spectral dynamics during wakefulness.

It is also useful to be able to identify non-quiescent wakefulness common at the early stages of a sleep study or experiment. FIG. 9B shows the occipital multitaper spectrogram for a different subject during a restless period of waking drowsiness. Overall, this period shows a mix of eyes open wakefulness and transient alpha with broadband background noise. Additionally, strong subject movement appears in the spectrogram as vertical lines spanning across all frequencies. While these motion artifacts are not part of the EEG signal, they provide important information regarding the quiescence of the subject during wakefulness. Motion artifacts are also important during sleep, as they appear with less power accompanying arousals throughout the night (see FIG. 9A at the moment of arousal).

Clinically, NREM sleep is divided into three stages (N1-N3) using semantic thresholds on the degree of observed delta, theta, and slow wave activity, as well as on the presence of spindles and K-complexes. While these guidelines provide simple rules by which to categorize degrees of NREM sleep by eye, a great deal of information is lost by limiting NREM to only three possible states, which evolve through instantaneous transition. In contrast, the multitaper spectrogram reveals the information-rich continuum of spectral dynamics of NREM sleep, providing a robust visual and quantitative framework for understanding the activity, interactions, and neural mechanisms of the underlying oscillations.

Figure 10A:
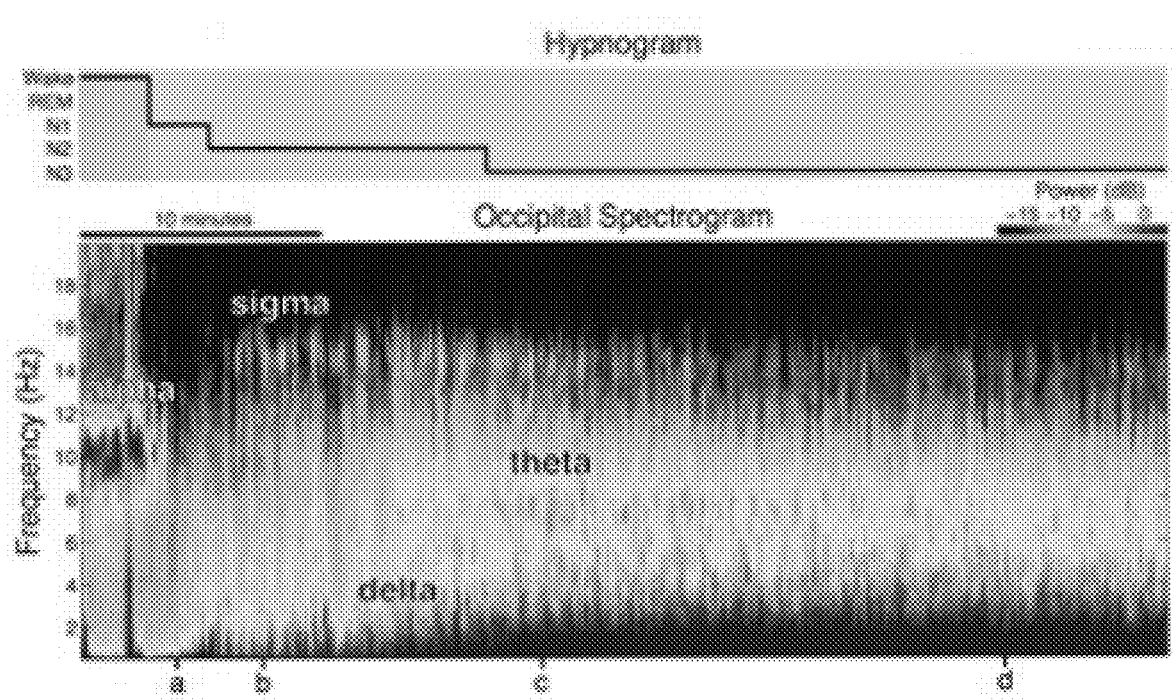
FIG. 10A is a graphical example illustrating spectral dynamics during NREM progression into slow wave sleep.
Figure 10B:
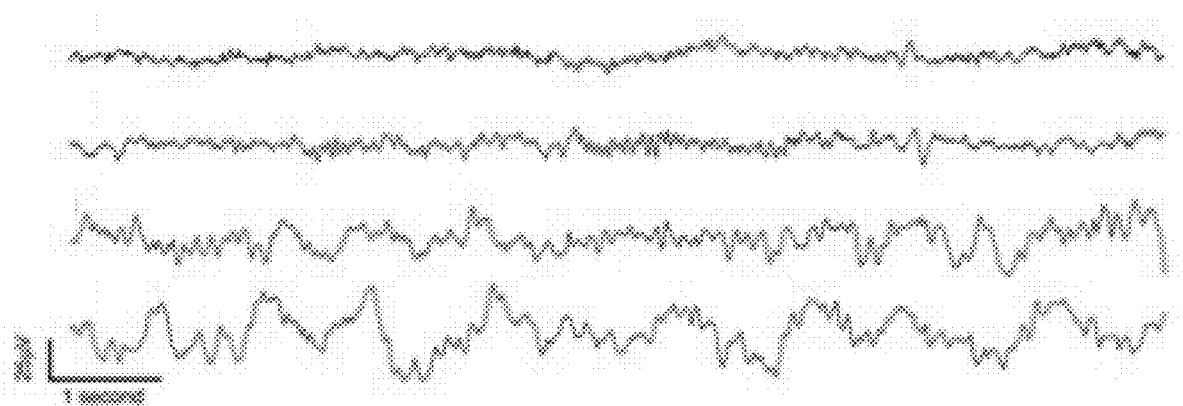
FIG. 10B shows waveform EEG data corresponding to different time points for the spectrogram of FIG. 10A.

FIG. 10A shows the occipital multitaper sleep spectrogram from a subject during the progression from scored Wake to Stage N1, N2, and N3. During this progression, the continuous dynamics of oscillations in alpha, delta, sigma, and theta. Time-domain traces are shown in FIG. 10B. Initially, just as in FIG. 9A, the subject goes through the sleep onset process, in which strong power in alpha transitions to broadband low frequency power at the start of scored Stage N1. This broadband oscillation has a sharp peak near 1 Hz, and grows continuously in both amplitude and bandwidth during the progression of NREM sleep. Shortly after the onset of the low broadband power, the spindle-related oscillation in sigma appears, corresponding with the scored Stage N2. As NREM progresses, power in sigma gradually decreases in both amplitude and bandwidth. Around the time of scored Stage N3, a spectral peak in theta power appears, which also decreases in power and bandwidth as NREM continues. Overall, FIG. 10A illustrates the principal spectral motif of NREM sleep, which can be seen repeated throughout the night in variation. This knowledge can therefore be used to characterize larger scale NREM dynamics and sleep fragmentation.

Figure 10C:
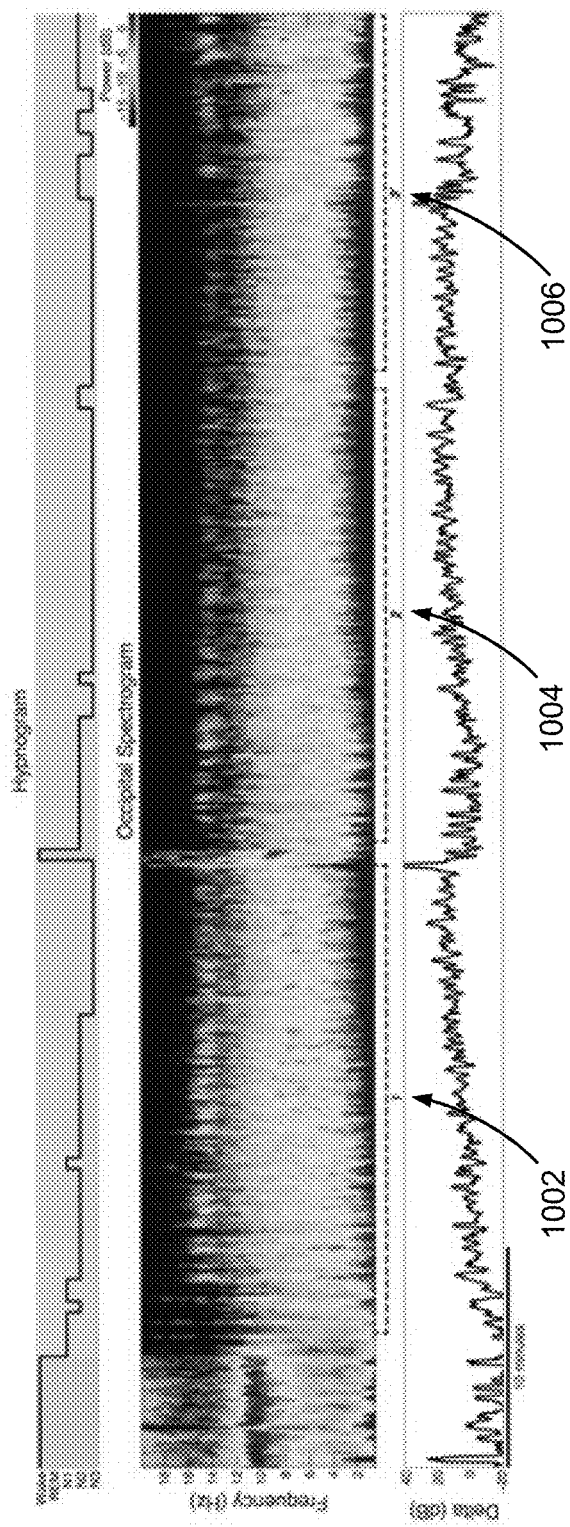
FIG. 10C is another graphical example illustrating spectral dynamics during NREM progression into slow wave sleep.

FIG. 10C shows the occipital multitaper spectrogram from a different subject during a disrupted bout of NREM. In this example, the NREM spectral motif is repeated three times, aligning well with both the hypnogram (top panel) and total observed delta power dynamics (bottom panel). The first motif appears during the sleep onset process, in which eyes closed alpha transitions to the oscillations of NREM sleep [FIG. 10C, Repetition 1, as indicated by arrow 1002]. As the power in sigma and theta start to decline, the subject has an arousal to wakefulness, marked by a motion artifact followed by a short burst of power in alpha. The oscillation in delta immediately resets to low power and small bandwidth, and then the NREM process starts again for the second time [FIG. 10C, Repetition 2, as indicated by arrow 1004]. A subsequent reduction in delta oscillation power and bandwidth indicates a lightening of NREM sleep, often linked to a scored arousal. If there is progressive lightening of sleep the same spectral dynamics of NREM motif can be seen, but in reverse. In this case, the subject lightens [FIG. 10C, Repetition 3, as indicated by arrow 1006], power in delta gradually decreases, while power in theta and sigma start to appear again.

Thus, by understanding the progression of oscillation dynamics during a single, uninterrupted bout of NREM, it becomes straightforward to characterize the general course and fragmentation of NREM throughout the entire evening.

A spindle is clinically defined as an 11-16 Hz frontal-central oscillation lasting 0.5 seconds or more. The broadness of this definition and the difficulty of visually gauging the precise oscillation frequency in the time domain make scoring of spindles extremely time-consuming and variable. Moreover, there is cross-subject heterogeneity in spindle morphology, which makes the creation of a one-size-fits-all automated classifier unfeasible. The multitaper spectrogram, however, provides a clear picture of the putative spindles that comprise transient sigma band activity.

Figure 11A:
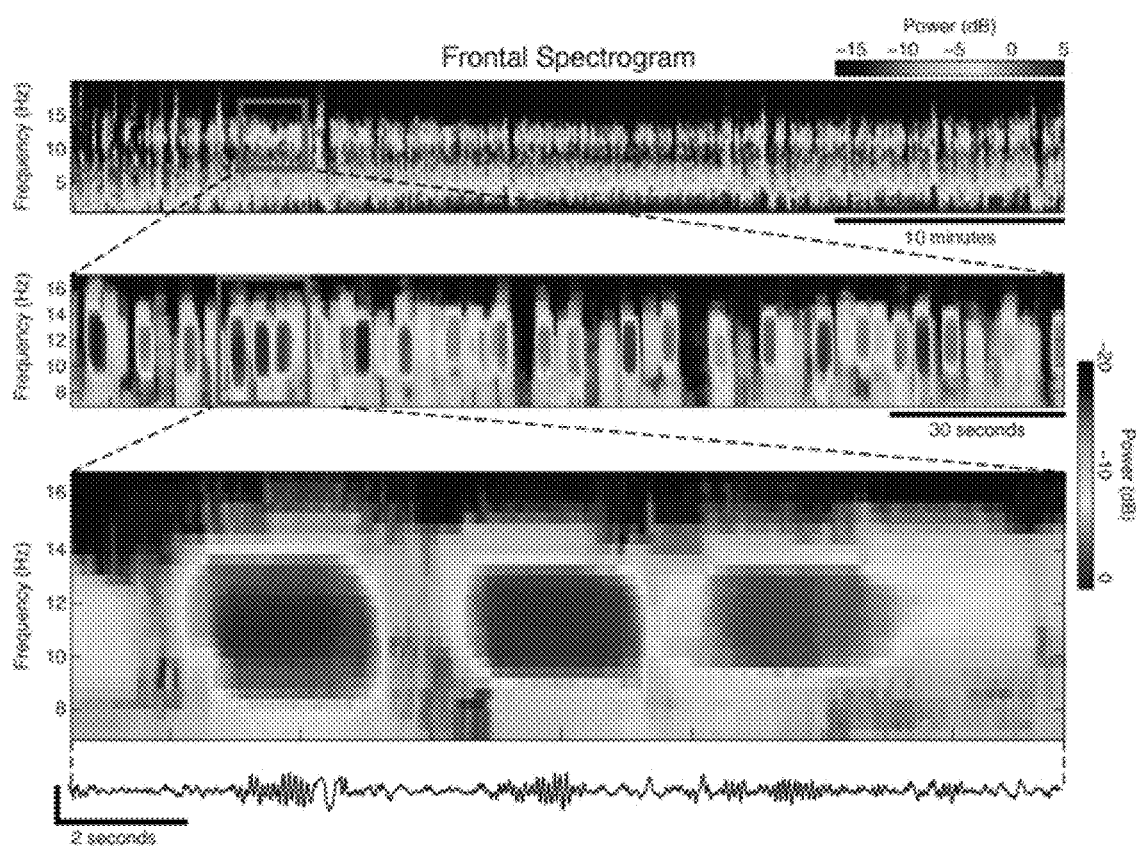
FIG. 11A is a graphical example illustrating multitaper spectrogram spindle activity.
Figure 11B:
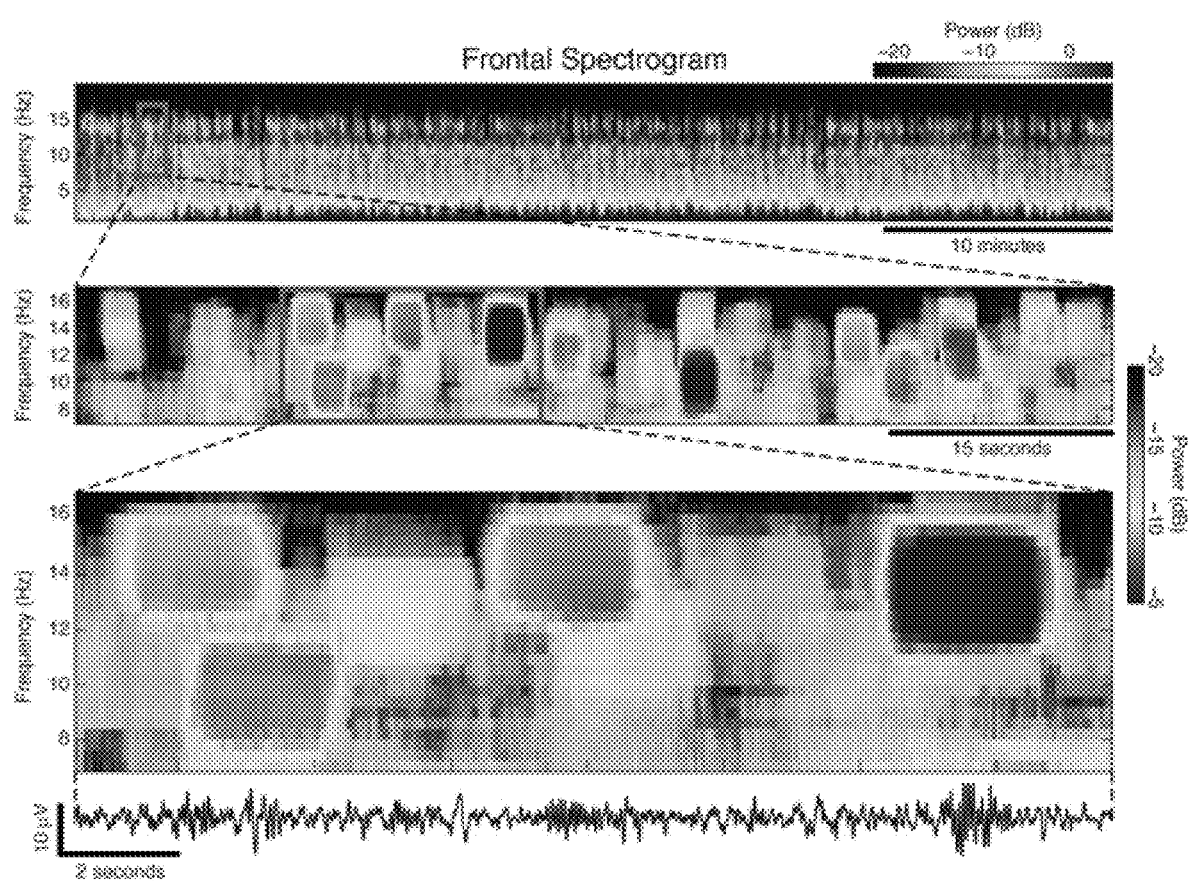
FIG. 11B is another graphical example illustrating multitaper spectrogram spindle activity.

Referring specifically to FIGS. 11A-B, examples of the frontal multitaper spectrogram of two different subjects during NREM are shown. The sigma band appears to be a cohesive oscillation at a time scale of tens of minutes (top panels) or more. However, when examining on at a time scale of a few minutes, it becomes clear that the sigma band power is comprised of many spindles, which appear in the spectrogram as well-defined transient peaks of spectral power (middle panels). On a time scale of a few seconds, the central frequency and duration of the spindle spectral peaks can be readily discerned and align well with time domain (bottom panels). While traditional time domain spindle scoring is the most straightforward in subjects with clear consistent spindles [FIG. 11A], it is much more difficult to visually discern spindles in subjects in which the morphology is highly variable or with the superposition of "fast" and "slow" spindles [FIG. 11B]. In contrast, the multitaper spectrogram representation can be easily interpreted regardless of the variability in spectral morphology, as the frequency decomposition provides a clear separation between spectral peaks of different frequencies.

Figure 12:
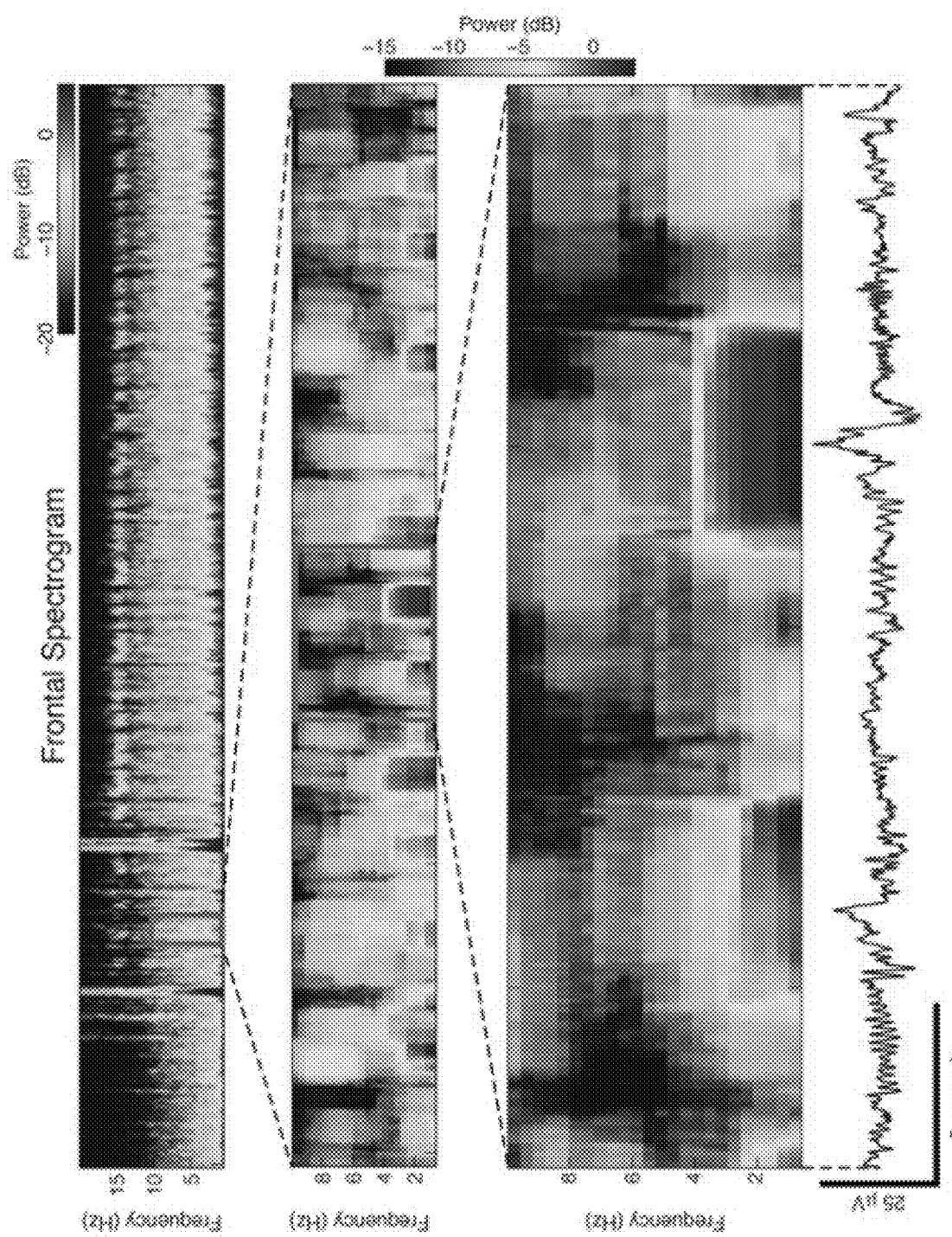
FIG. 12 is a graphical example illustrating multitaper spectrogram K-complex activity.

Similarly, K-complexes may be discerned from multitaper spectrograms as broadband power in low frequencies. FIG. 12 shows the occipital multitaper spectrogram of K-complexes occurring during NREM, which are aligned with the time domain trace. K-complexes may be readily distinguished from motion artifacts, as the spectral power quickly attenuates by 2-3 Hz, and the duration is shorter.

While this assortment of multi-modal observations comprising REM sleep suggests a plurality of evolving processes, REM is scored as a unitary state into which the subject instantly transitions. The multitaper EEG spectrogram reveals that the neural activity spanning traditionally defined REM to be a progression of oscillatory changes through the subject gradually transitions.

Figure 13A:
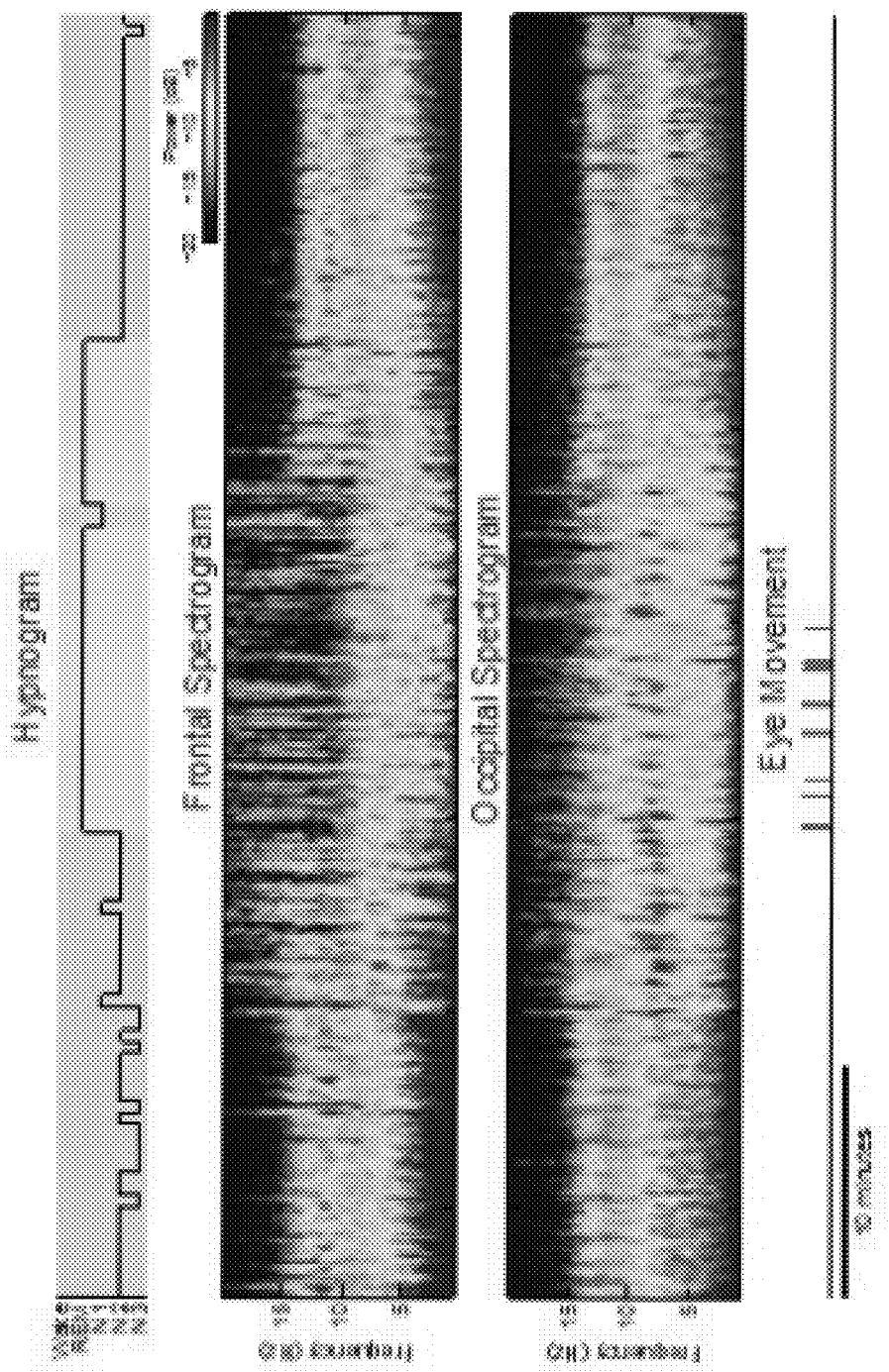
FIG. 13A is a graphical example of a multitaper spectrogram showing EEG spectral dynamics during REM in frontal and occipital locations.

FIG. 13A shows 60 minutes of the frontal (top panels) and occipital (middle panels) multitaper spectrum from a different subject going from NREM to REM then back to NREM. While the hypnogram depicts a series of instantaneous transitions, the multitaper spectrogram shows gradual changes in the EEG activity during this period. The spectral motif of a gradually lightening out of NREM is first observed (similar to FIG. 10A) with low frequency power decreasing and power in sigma increasing.

The multitaper spectrogram provides a computational basis with which to visualize at the sleep EEG on a larger time scale than the time domain, which makes it possible to observe phenomena not readily apparent in 30-second epochs. In FIG. 13A, as NREM lightens, the occipital spectrogram shows transient increases in occipital power in low-alpha frequencies. These peri-REM bursts appear to last up to 30 seconds, and with an increasing interburst interval as throughout period of scored REM. During this time, the power in sigma, delta, and theta drop off precipitously. Noteworthy is that that the power in these bands appears to be higher than during eyes closed alpha. This progression of spectral dynamics then reverses itself, with the periodic occipital peaks decreasing in frequency, and gradually returning to the standard NREM spectral motif.

Figure 13B:
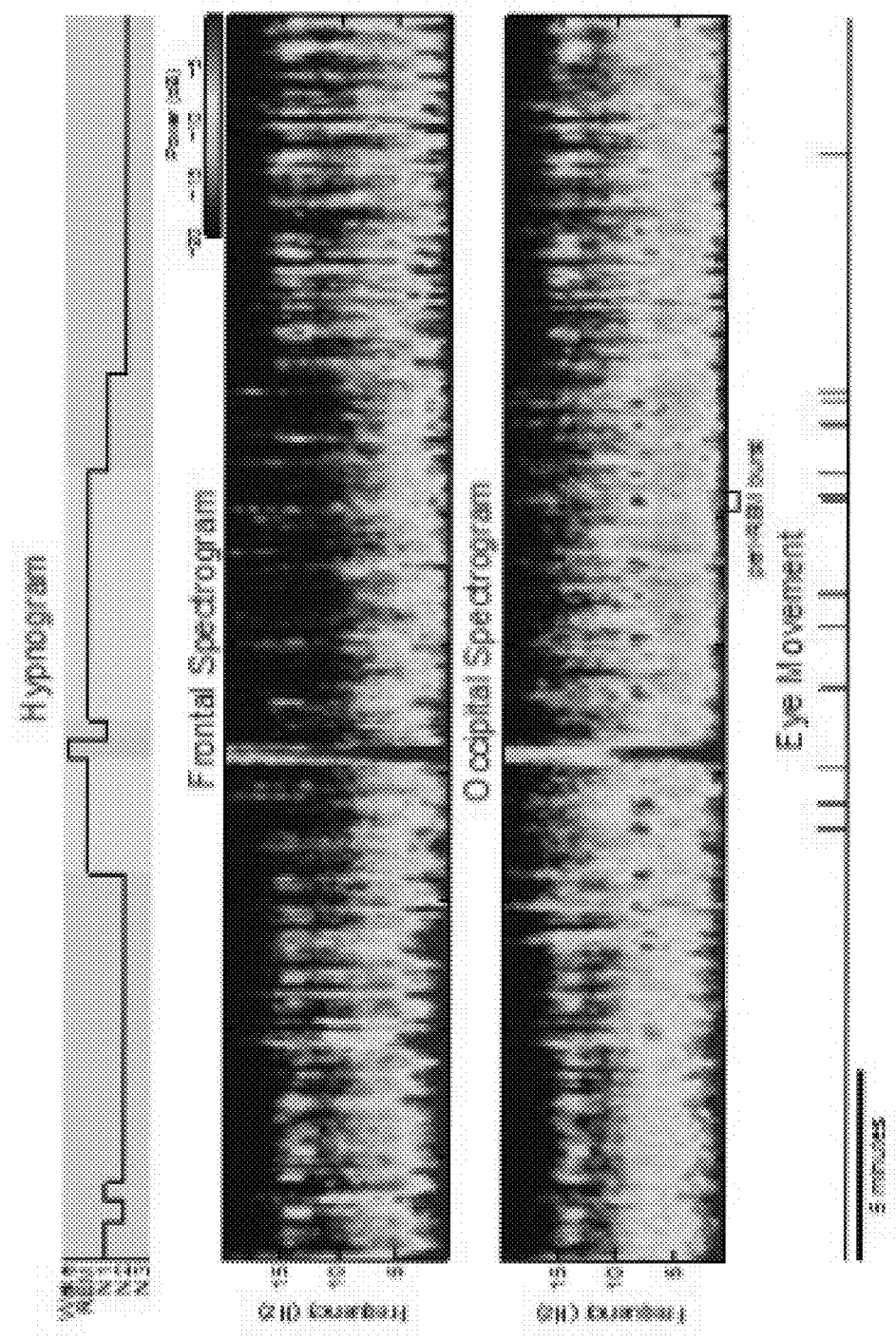
FIG. 13B is another graphical example of a multitaper spectrogram showing EEG spectral dynamics during REM in frontal and occipital locations.

FIG. 13B shows the period surrounding a bout of scored REM for another subject, but on a time scale of 30 minutes. At this scale, it is possible to see the seemingly periodic nature of occipital activity in low-alpha. The motion artifact indicates a brief arousal, though the dynamics of the EEG seem little changed afterwards.

Overall, the observed peri-REM spectral motif of transient power in occipital low-alpha consistently contains scored REM sleep, but often precedes or extends the bounds of scored REM by several minutes. Plotting the times of rapid eye movements against the spectrogram [FIG. 13A-B, bottom panels] shows a correlation between such movements and features on the observed spectrogram.

Given the spectral motifs observed around scored Wake, NREM, and peri-REM epochs, it is possible to quickly characterize the sleep EEG from the full-night occipital multitaper spectrogram, as shown in the example multitaper spectrogram of FIG. 8A. Signatures of non-quiescent wakefulness are observed [FIG. 9B], followed by waking power in alpha [FIG. 9A]. Sleep onset process is also observed, in which power in alpha transitions to the NREM spectral motif [FIG. 10A] at around 1:00 into the recording. By examining the changes in power and bandwidth in delta and theta, along with the corresponding changes in sigma, the dynamics of the fragmentation in NREM can be readily discerned [FIG. 10C]. After deepening, lightening, and deepening in NREM again (~1:00-3:00), the EEG transitions into the peri-REM spectral motif (~3:00-3:30), with the periodic peaks in alpha and reduced low frequency power [FIG. 13A]. Note that the low frequency power is visibly higher than during eyes closed alpha, and that the power in alpha itself is non-periodic during wakefulness and thus appears more vividly in the spectrogram. The EEG then successively transitions between NREM and peri-REM motifs four more times (~3:30-9:30), with a period of wakeful power in alpha in the last of the NREM bouts (~8:30). Through examining the changes in spectral power during each of these NREM periods, it is possible to describe the differences in duration fragmentation at a more precise level if required. The final motif of NREM activity changes to an eyes closed alpha followed by a mixed period of quiescent and non-quiescent wakefulness as the subject wakes up (~9:30-10:30). Throughout the recording, motion artifacts can be seen as faint vertical lines, providing insight into arousals and lightening of NREM sleep.

The same exercise can be performed with the subject in FIG. 8B. The night starts with a mixed period of eyes closed wakefulness and non-quiescent wakefulness (~0-1:00). A NREM to peri-REM to NREM motif transition is next (~1:00-2:30), followed by a period of eyes-closed wakefulness (~2:30-2:45). Next follows 3 NREM to peri-REM motif transitions (~2:45-8:00), interspersed with motion artifacts, which indicate periods of arousal or lightened sleep. A period of wakefulness (~8:00-8:10) is followed by NREM fragmented by a motion artifact (~8:10-8:45), after which the subject awakens for the rest of the period.

The approach described herein can be used to facilitate traditional sleep scoring by providing an assessment of metrics such as total sleep time ("TST") for use in clinical or experimental procedures. For example, this approach could be used in some clinical applications such as the multiple sleep latency test ("MSLT") for insomnia or split-night studies for characterizing apnea, in which TST is used to determine further clinical action or a diagnosis. Additionally, the approach could be used to estimate TST for the computation of specific clinical diagnostic metrics such as the apnea-hypopnea index ("AHI") or the reparatory disturbance index ("RDI"). Additionally, the visualization of the multitaper spectrogram may replace or complement the use of the hypnogram in clinical or experimental procedures or reports.

Figure 14A:
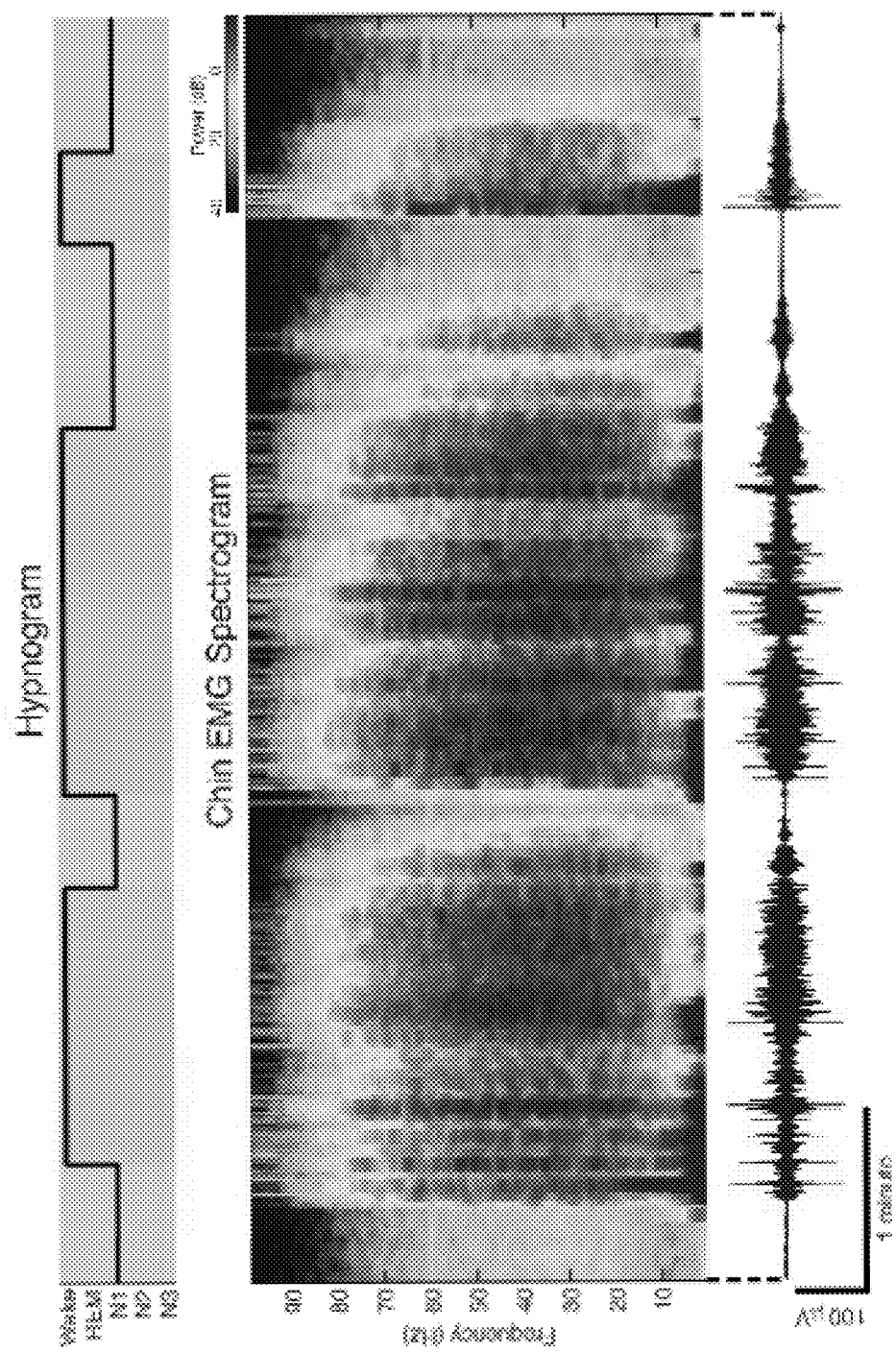
FIG. 14A is a graphical example of a multitaper spectrogram showing spectral dynamics of a healthy individual.
Figure 14B:
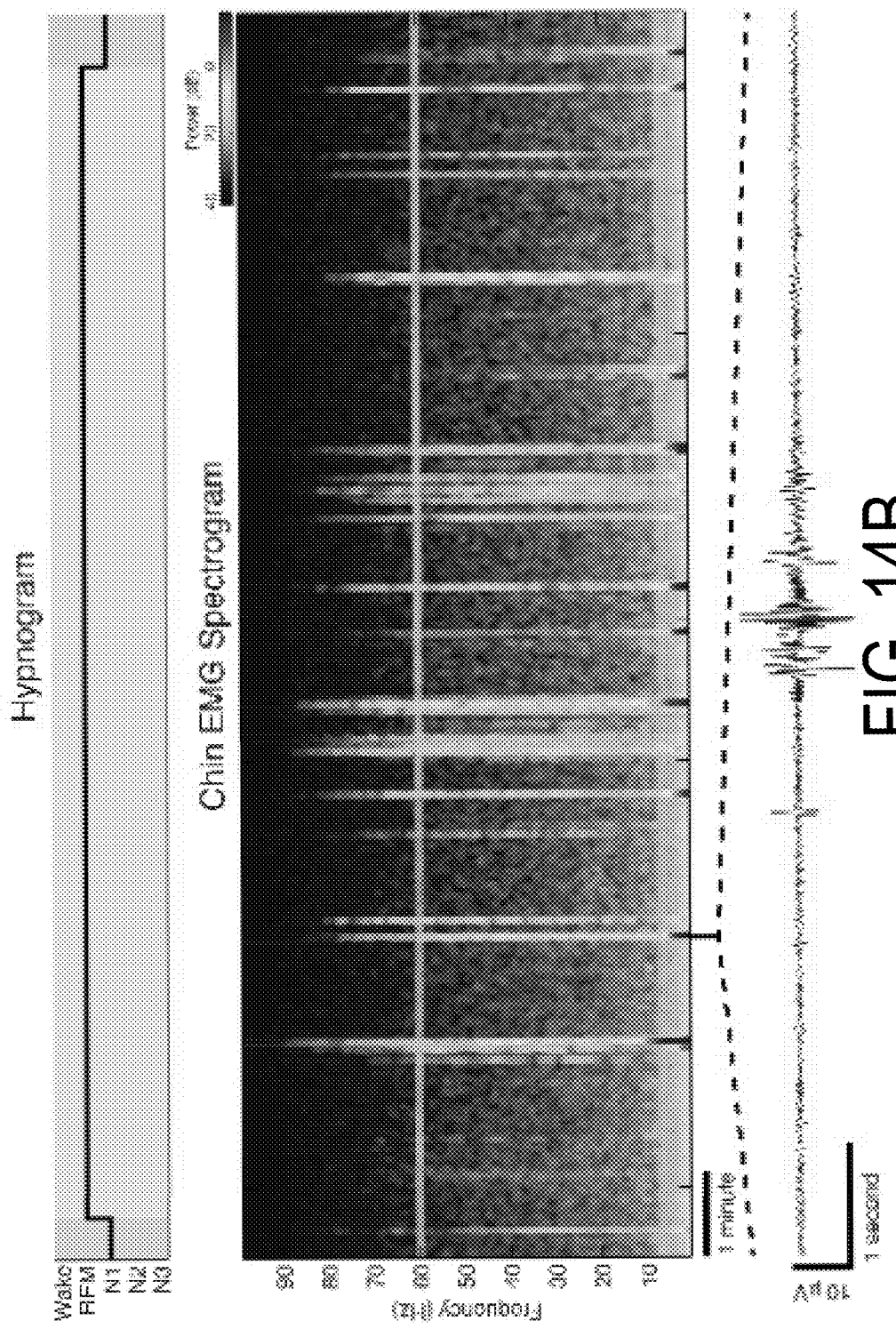
FIG. 14B is a graphical example of a multitaper spectrogram showing spectral dynamics of an individual with a neurodegenerative disorder.

The approach described herein can also be used to identify changes in sleep architecture, spectral composition, or other factors as a function of age, or as a function of mental health disorders including depression, schizophrenia, post-traumatic stress syndrome, bipolar disorder, or other psychiatric disorders or as a function of neurological disorders as Parkinson's disease, Huntington's disease, Alzheimer's disease, traumatic brain injury, or other neurological or neurodegenerative disorders. For example, FIG. 14A shows a multitaper spectrogram of a healthy individual, while FIG. 14B shows the multitaper spectrogram of a patient with a neurodegenerative disorder. As shown, multitaper spectrogram makes clear the difference in sleep architecture and spectral composition of between the sleep EEG of the healthy subject and that of the subject with the neurodegenerative disorder. This suggests that multitaper spectrograms, in accordance with the present disclosure, can be a vital tool in the assessment of mental health as well as the diagnosis and characterization of neurological disorders.

Additionally, the above approach can also be used to identify changes in sleep architecture, spectral composition, or other factors as a function of pharmacological agents, for example zaleplon, zolpidem, triazolam, ramelteon, or eszopiclone. For example, the effects of a drug could be assessed using changes in the multitaper sleep spectrogram as a function of the administration of the pharmacological agent.

Although the above approach has been described in terms of analyzing EEG data, multitaper spectrograms can be computed to characterize other signals related to sleep. For example, the multitaper spectrogram can be used to characterize muscle activity during sleep using electromyography ("EMG") sensors. FIGS. 15A-B shows examples of chin EMG activity during wake (FIG. 15A) and REM sleep stage (FIG. 15B). In standard clinical analyses, 30-second epochs of the chin EMG time domain trace are used to help identify different sleep stages. In the above examples, multitaper spectrograms computed in accordance with the present disclosure clearly illustrates the difference between waking EMG activity, which consists of sustained increases in muscle tone, and EMG activity during REM, which consists of short intermittent pulses of muscle tone. The differences in the spectrograms can be used in conjunction with the EEG and other signals to easily disambiguate between Wake and REM periods on both short and long time scales. In addition, multitaper spectrograms may be computed for other signals including but not limited to galvanic skin response, respiration, ECG and other autonomic metrics, actigraphy, or any other signal related to sleep.

In summary, the present disclosure provides a system and method for characterizing sleep. The approach described allows for identifying dynamical signatures associated with the sleep EEG data, and hence could provide critical insight into the neural processes occurring during sleep, aiding in both diagnosis and in treatment of different medical conditions. The present approach can be utilized for manual visual sleep scoring, as a display for analysis, or for quickly estimating total sleep time for clinical applications. In addition, the present system and method can also be used for diagnosing disease, such as neurological or psychiatric disease, as well as pathophysiology, or as a basis for characterizing the effect of pharmaceuticals, such as those intended to treat sleep disorders, or those that may disrupt sleep. Furthermore, the present system and method can be applied to determine sleep quality, sleep hygiene or fitness level.

As may be appreciated, the provided system and method may be implemented in a variety of systems and devices. For instance, some implementations can includes systems and devices for research or commercial laboratory sleep monitoring, for home sleep monitoring, as well as a number of commercial products, such as self-improvement or fitness applications, including wearable consumer products or mobile devices.

The present invention has been described in terms of one or more preferred embodiments, and it should be appreciated that many equivalents, alternatives, variations, and modifications, aside from those expressly stated, are possible and within the scope of the invention.

The invention claimed is:

1. A system for identifying sleep states of a subject, the system comprising:
a plurality of sensors configured to acquire at least electroencephalogram ("EEG") data from a subject; and
a processor configured to:
   i) assemble the EEG data received from the plurality of sensors over a sleep period into time-series datasets;
   ii) select a temporal window in which signals associated with the time-series datasets are substantially spatially invariant;
   iii) compute a time bandwidth product based on a selected spectral resolution and the selected temporal window;
   iv) determine a number of tapers using the computed time bandwidth product;
   v) compute a multitaper spectrogram using the time bandwidth product, the determined number of tapers, and the temporal window to make the time-series datasets substantially spatially invariant;
   vi) analyze the multitaper spectrogram to identify signatures indicative of sleep states of the subject; and
   vii) generate, using the identified signatures from the multitaper spectrogram analysis, a report indicative of sleep states of the subject characterizing neural states of the subject over the sleep period, wherein an effect of a drug is assessed using changes in the multitaper spectrogram as a function of administering pharmacological agents.

2. The system of claim 1, wherein the plurality of sensors is further configured to acquire physiological data from the subject corresponding to at least one of a brain activity, a muscle activity, a respiration activity, a cardiac activity, an eye movement, a galvanic skin response, a movement, a blood oxygenation, or combinations thereof.

3. The system of claim 1, wherein the sleep period includes one of a full night time scale, an ultradian time scale, or a micro-event time scale.

4. The system of claim 1, wherein the processor is further configured to analyze the multitaper spectrogram to identify non-stationary dynamics within one or more frequency bands, including an alpha band, a sigma band, a theta band, a delta band, a slow wave band, a beta band, and a gamma band.

5. The system of claim 1, wherein the processor is further configured to detect at least one of a spindle oscillation, a K-complex, an arousal, a burst, or a transient oscillation.

6. The system of claim 1, wherein the processor is further configured to generate a multinomial model using information obtained from the multitaper spectrogram computed at step v).

7. The system of claim 1, wherein the processor is further configured to track the identified signatures in time using the multitaper spectrogram.

8. The system of claim 1, wherein the processor is further configured to identify a condition of the subject using the identified signatures.

9. The system of claim 1, wherein the processor is further configured to determine an effectiveness of a pharmacological agent using the identified signatures.

10. The system of claim 1, wherein the processor is further configured to determine a sleep fragmentation using the multitaper spectrogram.

11. A method for identifying sleep states of a subject, the method comprising:
a) acquiring at least electroencephalogram ("EEG") data from a subject over a sleep period using sensors positioned about the subject;
b) assembling the EEG data into time-series datasets;
c) selecting a temporal window in which signals associated with the time-series datasets are substantially spatially invariant;
d) computing a time bandwidth product based on a selected spectral resolution and the selected temporal window;
e) determining a number of tapers using the computed time bandwidth product;
f) computing a multitaper spectrogram using the time bandwidth product, the determined number of tapers, and the temporal window to make the time-series datasets substantially spatially invariant;
g) analyzing the multitaper spectrogram to identify signatures of sleep in the subject; and h) generating, using the identified signatures from the multitaper spectrogram analysis, a report indicative of sleep states of the subject, wherein an effect of a drug is assessed using changes in the multitaper spectrogram as a function of administering pharmacological agents.

12. The method of claim 11, wherein the method further comprises acquiring physiological data from the subject corresponding to at least one of a brain activity, a muscle activity, a respiration activity, a cardiac activity, an eye movement, a galvanic skin response, a movement, a blood oxygenation, or combinations thereof.

13. The method of claim 11, wherein the sleep period includes one of a full night time scale, an ultradian time scale, or a micro-event time scale.

14. The method of claim 11, wherein the method further comprises analyzing the multitaper spectrogram to identify non-stationary dynamics within one or more frequency bands, including an alpha band, a sigma band, a theta band, a delta band, a slow wave band, a beta band, and a gamma band.

15. The method of claim 11, wherein the method further comprises detecting at least one of a spindle oscillation, a K-complex, an arousal, a burst, or a transient oscillation.

16. The method of claim 11, wherein the method further comprises generating a multinomial model using information obtained from the multitaper spectrogram.

17. The method of claim 11, wherein the method further comprises tracking the identified signatures in time using the multitaper spectrogram.

18. The method of claim 11, wherein the method further comprises identifying a condition of the subject using the identified signatures.

19. The method of claim 11, wherein the method further comprises determining an effectiveness of a pharmacological agent using the identified signatures.

20. The method of claim 11, wherein the method further comprises determining a sleep fragmentation using the multitaper spectrogram.

21. The method of claim 11, wherein the method further comprises computing a wakefulness probability using information obtained from the multitaper spectrogram.

* * * * *